US 12,254,046 B2

(12) United States Patent
Schilders

(10) Patent No.: US 12,254,046 B2
(45) Date of Patent: Mar. 18, 2025

(54) IN-SITU DATA PROCESSING IN OVERLAY SYSTEMS USING MICRO-OVERLAYS

(71) Applicant: INFOSYS LIMITED, Bangalore (IN)

(72) Inventor: Steven Schilders, Columbus, IN (US)

(73) Assignees: Infosys Limited, Bangalore (IN); InvertIT Inc., Columbus, IN (US)

( * ) Notice: Subject to any disclaimer, the term of this patent is extended or adjusted under 35 U.S.C. 154(b) by 0 days.

(21) Appl. No.: 18/589,308

(22) Filed: Feb. 27, 2024

(65) Prior Publication Data

US 2024/0289393 A1   Aug. 29, 2024

Related U.S. Application Data

(60) Provisional application No. 63/448,738, filed on Feb. 28, 2023, provisional application No. 63/448,831, filed on Feb. 28, 2023, provisional application No. 63/448,757, filed on Feb. 28, 2023, provisional application No. 63/448,724, filed on Feb. 28, 2023, provisional application No. 63/448,711, filed on Feb. 28, 2023.

(51) Int. Cl.
*G06F 7/02* (2006.01)
*G06F 16/00* (2019.01)
*G06F 16/901* (2019.01)
*G16H 10/60* (2018.01)

(52) U.S. Cl.
CPC ......... *G06F 16/9024* (2019.01); *G16H 10/60* (2018.01)

(58) Field of Classification Search
CPC .......................... G06F 16/9024; G16H 10/60
See application file for complete search history.

(56) References Cited

U.S. PATENT DOCUMENTS

| | | | |
|---|---|---|---|
| 2021/0365457 A1* | 11/2021 | Venema | G06F 16/248 |
| 2022/0043973 A1* | 2/2022 | Arroyo | G06F 40/237 |
| 2024/0202192 A1* | 6/2024 | Liang | G06F 16/9024 |
| 2024/0362274 A1* | 10/2024 | Agassi | G06F 16/906 |

* cited by examiner

*Primary Examiner* — Bruce M Moser
(74) *Attorney, Agent, or Firm* — Finnegan, Henderson, Farabow, Garrett & Dunner, LLP

(57) ABSTRACT

An overlay system including a storage element and processing circuitry is provided. The storage element stores an executable graph-based model that includes various active nodes and various micro-overlay nodes. Further, each active node includes multiple node elements, where each micro-overlay node is associated with at least one node element, and extends the functionality of the corresponding node element. The processing circuitry receives a contextualized stimulus. Further, the processing circuitry identifies an active node, node elements of the active node associated with the processing of the contextualized stimulus, and one or more micro-overlay nodes associated with each identified node element. The processing circuitry executes an operation associated with the contextualized stimulus based on the identified node elements and one or more micro-overlay nodes associated with each identified node element.

20 Claims, 14 Drawing Sheets

IN-SITU DATA PROCESSING IN OVERLAY SYSTEMS USING MICRO-OVERLAYS

CROSS-REFERENCE TO RELATED APPLICATIONS/INCORPORATION BY REFERENCE

This patent application refers to, claims priority to, and claims the benefit of U.S. Provisional Application Ser. Nos. 63/448,738, filed Feb. 28, 2023; 63/448,724; filed Feb. 28, 2023; 63/448,831, filed Feb. 28, 2023; 63/448,711, filed Feb. 28, 2023; and 63/448,757, filed Feb. 28, 2023. Each of the above-referenced applications is hereby incorporated herein by reference in its entirety.

FIELD OF THE DISCLOSURE

Various embodiments of the present disclosure relate generally to data processing. More specifically, various embodiments of the present disclosure relate to in-situ data processing in overlay systems using micro-overlays.

BACKGROUND

In the present era, data plays a crucial role in numerous domains (for example, research and development, marketing, service provider platforms, or the like). Traditionally, such domains have system designs that involve storing data associated therewith in corresponding databases. In order to perform an operation using data stored in a database, a corresponding processing logic is applied to the stored data. Notably, the data and processing logic are stored separately using corresponding storage techniques and are required to interact with each other to facilitate the execution of the operation. This leads to a significant increase in processing complexity and time complexity associated with the execution of the operation, which is undesirable. In some scenarios, the operation may be time-critical, and hence, such a significant increase in the processing complexity and the time complexity may have an adverse impact on one or more time-critical applications (such as medical devices, autonomous vehicles, real-time control systems, or the like) associated with the operation.

In light of the foregoing, there exists a need for a technical and reliable solution that overcomes the abovementioned problems.

Limitations and disadvantages of conventional and traditional approaches will become apparent to one of skill in the art, through the comparison of described systems with some aspects of the present disclosure, as set forth in the remainder of the present application and with reference to the drawings.

SUMMARY

Methods and systems for in-situ data processing in overlay systems using micro-overlays are provided substantially as shown in, and described in connection with, at least one of the figures.

These and other features and advantages of the present disclosure may be appreciated from a review of the following detailed description of the present disclosure, along with the accompanying figures in which like reference numerals refer to like parts throughout.

BRIEF DESCRIPTION OF THE DRAWINGS

Embodiments of the present disclosure are illustrated by way of example and are not limited by the accompanying figures. Similar references in the figures may indicate similar elements. Elements in the figures are illustrated for simplicity and clarity and have not necessarily been drawn to scale.

DETAILED DESCRIPTION

Figure 1:
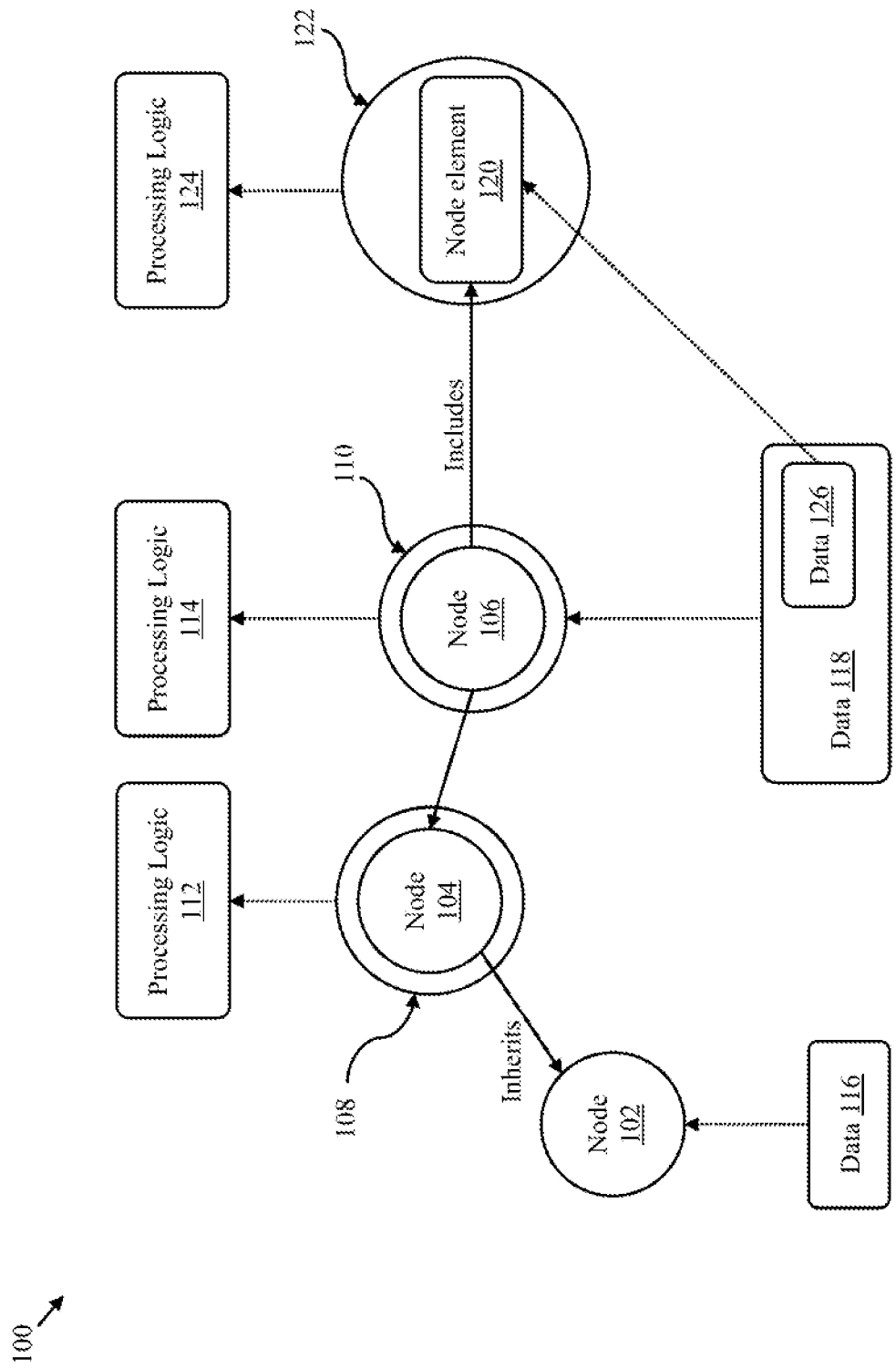
FIG. 1 is a graph that illustrates a composition of an executable graph-based model, in accordance with an embodiment of the present disclosure.

The detailed description of the appended drawings is intended as a description of the embodiments of the present disclosure and is not intended to represent the only form in which the present disclosure may be practiced. It is to be understood that the same or equivalent functions may be accomplished by different embodiments that are intended to be encompassed within the spirit and scope of the present disclosure.

Overview

Conventionally, data is stored in a database in the form of various data tables. Further, each data table includes data records, and each data record includes various related data elements. Processing logic is applied to one or more data tables to execute various operations associated with the database. The execution of processing logic on the one or more data tables utilizes only data records. However, some operations may require processing logic to be applied to particular data elements, which is not feasible with existing system designs. Additionally, the data records and processing logic are stored separately in conventional system designs. Thus, the conventional system design for data processing for various operations is not flexible and involves higher processing complexity and time complexity which is undesirable in time-critical operations.

The present disclosure is directed to the facilitation of in-situ data processing in overlay systems using micro-overlays. Executable graph-based models are stored in a storage element of an overlay system. The executable graph-based models are customized hypergraphs having hyperedges and vertices that are realized by way of active nodes. Each active node is associated with a particular node type. For example, an edge node corresponds to a node with an edge node type. Nodes are connected with other nodes by way of edge nodes (e.g., roles included in the edge nodes). In some embodiments, roles are represented by way of nodes of role node type. A role node between two nodes may be indicative of details regarding an association therebetween. The executable graph-based models further comprise macro-overlay nodes to extend the functionality of the nodes such as vertices and edges, with processing logic. Further, each active node corresponds to a data record of a database, and each active node includes node elements that correspond to data elements of the data record. Thus, the executable graph-based models further comprise micro-overlay nodes to extend the functionality of such node elements, with processing logic. Data (i.e., active nodes) and processing logic (i.e., micro and macro overlay nodes) are integrated at run-time in the overlay system. As a result, data processing in the overlay system is in-situ. Thus, processing and time complexities associated with data processing are significantly reduced.

In an example, the overlay system includes an executable graph-based model that includes various active nodes, various macro-overlay nodes associated with each active node, various node elements of each active node, and various micro-overlay nodes associated with the node elements of each active node. Each macro-overlay node is associated with at least one active node, and is configured to extend functionality of the corresponding active node with processing logic. Similarly, each micro-overlay node is associated with at least one node element, and is configured to extend functionality of the corresponding node element with processing logic. In operation, processing circuitry of the overlay system may receive a stimulus. The processing circuitry may identify, from the executable graph-based model at least a first active node based on a context of the stimulus. Further, based on the context of the stimulus, the processing circuitry may also identify one or more macro-overlay nodes associated with the first active node, one or more node elements of the first active node, and one or more micro-overlay nodes associated with each identified node element, that are required for processing the first stimulus. The processing circuitry executes an operation associated with the stimulus based on the first active node, the one or more macro-overlay nodes associated with the first active node, the one or more node elements of the first active node, and the one or more micro-overlay nodes associated with each identified node element.

Traditionally, data processing involves interaction between mutually segregated data and processing logic. Thus, any operation associated with data processing involves increased time complexity and processing complexity, as data and processing logic have to be separately accessed and combined for data processing. In contrast, the present disclosure provides an overlay system that stores an executable graph-based model where data and processing logic are integrated at run-time for data processing. Thus, the time complexity and processing complexity involved with data processing are significantly reduced. Additionally, in traditional approaches, the processing logic is applied to one or more data tables for executing an operation even though all data records present in the one or more data tables are not required for the execution of the operation. Also, there is no provision to apply processing logic only to data records and/or data elements in conventional database system designs. In contrast, in the disclosed overlay system, processing logic can be applied to various node elements associated with a node, thus extending the functionality of corresponding node elements. As a result, the overlay system is highly flexible.

Systems and methods for facilitating in-situ data processing in overlay systems using micro-overlays are provided. As data and processing logic are in situ in the overlay system at run-time, time complexities and processing complexities associated with data processing are significantly reduced. Additionally, the functionality of node elements (i.e., data elements) associated with nodes (i.e., data records) is extended by the use of micro-overlays in the overlay system. Thus, the overlay system is highly flexible as processing logic can be applied to desirable node elements and operations based on processing logic can be executed only on the desirable node elements. Further, the disclosed systems and methods do not require the data and processing logic to be available at all times, and hence, the data and processing logic, when not in use, may be stored separately and re-loaded in the corresponding executable node when needed. Thus, the systems and methods disclosed herein provide an efficient approach for in-situ data processing in overlay systems using micro-overlays.

Figure Description

FIG. 1 is a graph that illustrates a composition of an executable graph-based model 100, in accordance with an embodiment of the present disclosure. Referring to FIG. 1, the executable graph-based model 100 is generally formed of a data structure (e.g., a graph-based model or a graphical model) comprising a plurality of nodes 102-106 which can be functionally extended with processing logic via the use of macro-overlays. For example, as shown in FIG. 1, the nodes 104 and 106 are functionally extended with processing logic via the use of macro-overlays 108 and 110, respectively. Although not shown, it will be apparent to a person skilled in the art that the node 102 can be similarly extended with processing logic via the use of one or more macro-overlays. Each macro-overlay includes processing logic, such as processing logic 112 and 114 which are associated with the macro-overlays 108 and 110, respectively. At run-time, data, such as data 116 and 118, is associated with the nodes 102 and 106, respectively, of the executable graph-based model 100. Further, the macro-overlays 108 and 110 of the nodes 104 and 106, respectively, provide the functionality to respond to stimuli and interact with, manipulate, or otherwise process the data for facilitating in-situ data processing in overlay systems based on the stimuli. Further, the node 104 inherits the node 102, and hence, also inherits the data 116 which is associated with the node 102. In some embodiments, the node 102 may be extended to have one or more macro-overlays. In such embodiments, the node 104 may further inherit the macro-overlays of the node 102.

A node forms the fundamental building block of all executable graph-based models. A node may be an executable node. A node extended by way of a macro-overlay node forms an executable node. One or more nodes are extended to include macro-overlays in order to form the executable graph-based models. As such, the executable graph-based model 100 includes one or more nodes that can be dynamically generated, extended, or processed by one or more other modules within an overlay system (shown in FIG. 2). Further, each node in the executable graph-based model 100 may include one or more node elements. For the sake of ongoing discussion, the node 106 is shown to include a node element 120. Each micro-overlay is configured to extend the functionality of one or more node elements similarly as a macro-overlay extends the functionality of a node. Thus, the processing logic is associated with each micro-overlay. For example, the node element 120 is functionally extended via the use of a micro-overlay 122 and the micro-overlay 122 includes processing logic 124 which is associated therewith. At run-time, data, such as data 126 is associated with the node element 120. Additionally, the data 118 includes the data 126, as the node 106 includes the node element 120.

As such, the structure and functionality of the data processing are separate from the data itself when offline (or at rest) and are combined dynamically at run-time. The executable graph-based model 100 thus maintains the separability of the data and the processing logic when offline. Moreover, by integrating the data and the processing logic within a single model, processing delays or latencies are reduced because the data and the processing logic exist within the same logical system. Therefore, the executable graph-based model 100 is applicable to a range of time-critical systems where efficient processing of the stimuli is required. In an instance, the executable graph-based model 100 may be used for in-situ processing of stimuli such as a command, a query, or the like.

Figure 2:
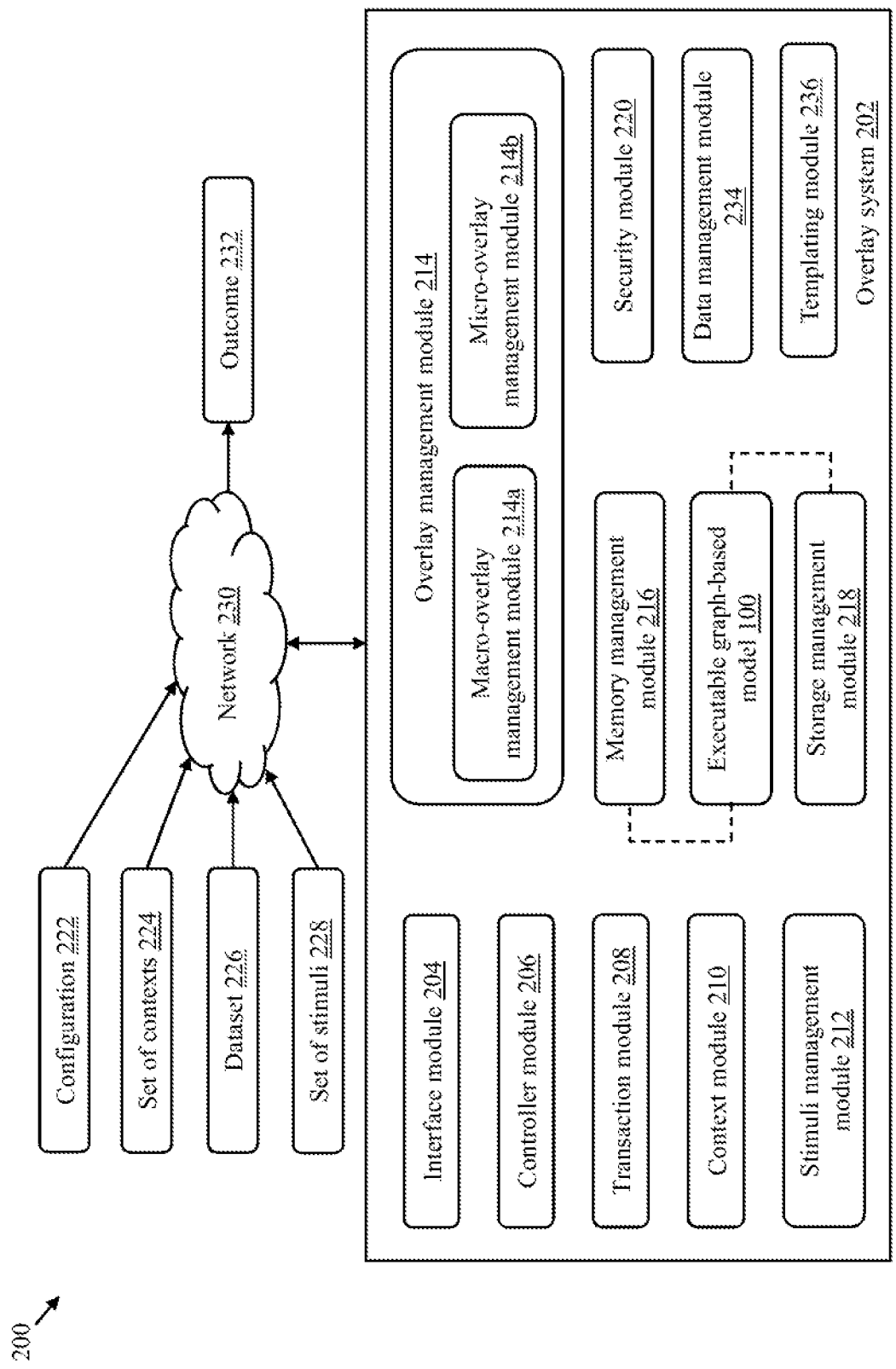
FIG. 2 is a block diagram that illustrates a system environment of an overlay system for execution, management, and configuration of the executable graph-based model, in accordance with an embodiment of the present disclosure.

FIG. 2 is a block diagram that illustrates a system environment 200 of an overlay system 202 for execution, management, and configuration of the executable graph-based model 100, in accordance with an embodiment of the present disclosure. Referring to FIG. 2, the overlay system 202 includes the executable graph-based model 100. The overlay system 202 further includes an interface module 204, a controller module 206, a transaction module 208, a context module 210, a stimuli management module 212, an overlay management module 214, a memory management module 216, a storage management module 218, and a security module 220. FIG. 2 further shows a configuration 222, a set of contexts 224, a dataset 226, a set of stimuli 228, a network 230, and an outcome 232.

The overlay system 202 may include suitable logic, circuitry, interfaces, and/or code, executable by the circuitry, that may be configured to facilitate in-situ data processing using executable graph-based models (such as the executable graph-based model 100). The executable graph-based model 100 corresponds to an application-specific combination of data and processing functionality which is manipulated, processed, and/or otherwise handled by other modules within the overlay system 202 for facilitating data processing based on the set of stimuli 228 received by the overlay system 202. Each stimulus in the set of stimuli 228 corresponds to a command, a query, or an event.

The interface module 204 may include suitable logic, circuitry, interfaces, and/or code, executable by the circuitry, configured to provide a common interface between internal modules of the overlay system 202 and/or external sources. The interface module 204 provides an application programmable interface (API), scripting interface, or any other suitable mechanism for interfacing externally or internally with any module of the overlay system 202. As shown in FIG. 1, the configuration 222, the set of contexts 224, the dataset 226, and the set of stimuli 228 are received by the interface module 204 via the network 230. Similarly, outputs produced by the overlay system 202, such as the outcome 232, are passed by the interface module 204 to the network 230 for consumption or processing by external systems. In one embodiment, the interface module 204 supports one or more messaging patterns or protocols such as the simple object access protocol (SOAP), the representational state transfer (REST) protocol, or the like. The interface module 204 thus allows the overlay system 202 to be deployed in any number of application areas, operational environments, or architecture deployments. Although not illustrated in FIG. 1, the interface module 204 is communicatively coupled (e.g., connected either directly or indirectly) to one or more other modules or elements within the overlay system 202 (such as the controller module 206, the context module 210, the executable graph-based model 100, or the like). In one embodiment, the interface module 204 is communicatively coupled (e.g., connected either directly or indirectly) to one or more macro-overlays and one or more micro-overlays within the executable graph-based model 100.

The controller module 206 may include suitable logic, circuitry, interfaces, and/or code, executable by the circuitry, configured to handle and process interactions and executions within the overlay system 202. As will be described in more detail below, stimuli (such as the set of stimuli 228) and their associated contexts (such as the set of contexts 224) provide the basis for all interactions within the executable graph-based model 100. Processing of such stimuli may lead to the execution of processing logic associated with one or more macro-overlays and one or more micro-overlays within the executable graph-based model 100. The processing of the stimuli within the overlay system 202 may be referred to as a system transaction. The processing and execution of stimuli (and associated overlay execution) within the overlay system 202 is handled by the controller module 206. The controller module 206 manages all received input stimuli and processes them based on a corresponding context. Each context determines the priority that is assigned to process the corresponding stimulus by the controller module 206 or the context module 210. This allows each stimulus to be configured with a level of importance and prioritization within the overlay system 202.

The controller module 206 may maintain the integrity of the modules within the overlay system 202 before, during, and after a system transaction. The transaction module 208, which is associated with the controller module 206, is responsible for maintaining the integrity of the overlay system 202 through the lifecycle of a transaction. Maintaining system integrity via the controller module 206 and the transaction module 208 allows a transaction to be rolled back in the event of an expected or unexpected software or hardware fault or failure. The controller module 206 is configured to handle the processing of the set of stimuli 228 and transactions through architectures such as parallel processing, grid computing, priority queue techniques, or the like. In one embodiment, the controller module 206 and the transaction module 208 are communicatively coupled (e.g., connected either directly or indirectly) to one or more macro-overlays and one or more micro-overlays within the executable graph-based model 100.

As stated briefly above, the overlay system 202 utilizes a context-driven architecture whereby the set of stimuli 228 within the overlay system 202 is associated with the set of contexts 224 which is used to adapt the handling or processing of the set of stimuli 228 by the overlay system 202. The handling or processing of the set of stimuli 228 is done based on the set of contexts 224 associated therewith. Hence, each stimulus of the set of stimuli 228 is considered to be a contextualized stimulus. Each context of the set of contexts 224 may include details such as username, password, access token, device information, time stamp, one or more relevant identifiers (IDs), or the like, that are required for processing of a corresponding stimulus of the set of stimuli 228 within the executable graph-based model 100. Each context within the overlay system 202 may be extended to include additional information that is required for the processing of the corresponding stimulus (e.g., a query or a command).

The context module 210 may include suitable logic, circuitry, interfaces, and/or code, executable by the circuitry, configured to manage the handling of contexts within the overlay system 202, and is responsible for processing any received contexts (e.g., the set of contexts 224) and translating the received context to an operation execution context. In some examples, the operation execution context is larger than the received context because the context module 210 supplements the received context with further information necessary for the processing of the received context. The context module 210 passes the operational execution context to one or more other modules within the overlay system 202 to facilitate in-situ data processing in the overlay system 202. Contexts within the overlay system 202 can be external or internal. While some contexts apply to all application areas and problem spaces, some applications may require specific contexts to be generated and used to process the received set of stimuli 228. As will be described in more detail below, the executable graph-based model 100 is configurable (e.g., via the configuration 222) so as only to execute within a given execution context for a given stimulus.

The stimuli management module 212 may include suitable logic, circuitry, interfaces, and/or code, executable by the circuitry, configured to process externally received stimuli (e.g., the set of stimuli 228) and any stimuli generated internally from any module within the overlay system 202. The stimuli management module 212 is communicatively coupled (e.g., connected either directly or indirectly) to one or more macro-overlays and one or more micro-overlays within the executable graph-based model 100 to facilitate the processing of stimuli within the executable graph-based model 100. The overlay system 202 utilizes different types of stimuli such as a command (e.g., a transactional request), a query, or an event received from an external system such as an Internet-of-Things (IoT) device. As previously stated, each stimulus of the set of stimuli 228 can be either externally or internally generated. In an example, each stimulus of the set of stimuli 228 may be a message that is internally triggered (generated) from any of the modules within the overlay system 202. Such internal generation of the set of stimuli 228 indicates that something has happened within the overlay system 202 such that subsequent handling by one or more other modules within the overlay system 202 may be required. An internal set of stimuli 228 can also be triggered (generated) from the execution of processing logic associated with overlays within the executable graph-based model 100. In another example, the set of stimuli 228 may be externally triggered and may be generated based on an input received via a user interface associated with the controller module 206. The externally triggered set of stimuli 228 may be received in the form of a textual, audio, or visual input. The externally triggered set of stimuli 228 may be associated with the intent of a user to execute a set of operations indicated by the set of stimuli 228. The operation is executed in accordance with the information included in the set of contexts 224 associated with the set of stimuli 228.

The stimuli management module 212 may receive the stimuli in real-time or near-real-time and communicate the received set of stimuli 228 to one or more other modules or nodes of the executable graph-based model 100. In some examples, the stimuli are scheduled in a batch process. The stimuli management module 212 utilizes any suitable synchronous or asynchronous communication architectures or approaches in communicating the stimuli (along with associated information). The stimuli within the overlay system 202 are received and processed (along with a corresponding context) by the stimuli management module 212, which then determines the processing steps to be performed for the execution of an operation associated with each stimulus of the set of stimuli 228. In one embodiment, the stimuli management module 212 processes the received stimuli in accordance with a predetermined configuration (e.g., the configuration 222) or dynamically determines what processing needs to be performed based on the contexts associated with the stimuli and/or based on a state of the executable graph-based model 100. The state of the executable graph-based model 100 refers to the current state of each node of the executable graph-based model 100 at a given point in time. The state of the executable graph-based model 100 is dynamic, and hence, may change in response to the execution of an operation based on any of its nodes. In some examples, the processing of each stimulus of the set of stimuli 228 results in the facilitation of in-situ data processing that further results in one or more outcomes being generated (e.g., the outcome 232). Such outcomes are either handled internally by one or more modules in the overlay system 202 or communicated via the interface module 204 as an external outcome. In one embodiment, all stimuli and corresponding outcomes are recorded for auditing and post-processing purposes by, for example, an operations module (not shown) and/or an analytics module (not shown) of the overlay system 202.

The overlay management module 214 may be configured to manage all overlays (e.g., macro-overlays and micro-overlays within the overlay system 202). Operations performed by the overlay management module 214 include overlay storage management, overlay structure modeling, overlay logic creation and execution, and overlay loading and unloading (within the executable graph-based model 100). The overlay management module 214 is shown to include a macro-overlay management module 214*a* and a micro-overlay management module 214*b*.

The macro-overlay management module 214*a* may include suitable logic, circuitry, interfaces, and/or code, executable by the circuitry, configured to manage all macro-overlays within the overlay system 202. Operations performed by the macro-overlay management module 214*a* include macro-overlay storage management, macro-overlay structure modeling, macro-overlay logic creation and execution, and macro-overlay loading and unloading (within the executable graph-based model 100). The macro-overlay management module 214*a* is communicatively coupled (e.g., connected either directly or indirectly) to one or more other modules within the overlay system 202 to complete some or all of these operations. For example, macro-overlays can be persisted in some form of physical storage using the storage management module 218 (as described in more detail below). As a further example, macro-overlays can be compiled and preloaded into memory via the memory management module 216 for faster run-time execution.

The micro-overlay management module 214*b* may include suitable logic, circuitry, interfaces, and/or code, executable by the circuitry, configured to manage all micro-overlays within the overlay system 202. Operations performed by the micro-overlay management module 214*b* include micro-overlay storage management, micro-overlay structure modeling, micro-overlay logic creation and execution, and micro-overlay loading and unloading (within the executable graph-based model 100). The micro-overlay management module 214*b* is communicatively coupled (e.g., connected either directly or indirectly) to one or more other modules within the overlay system 202 to complete some or all of these operations. For example, micro-overlays can be persisted in some form of physical storage using the storage management module 218 (as described in more detail below). As a further example, micro-overlays can be compiled and preloaded into memory via the memory management module 216 for faster run-time execution.

The memory management module 216 may include suitable logic, circuitry, interfaces, and/or code, executable by the circuitry, configured to manage and optimize the memory usage of the overlay system 202. The memory management module 216 thus helps to improve the responsiveness and efficiency of the processing performed by one or more of the modules within the overlay system 202 by optimizing the memory handling performed by these modules. The memory management module 216 uses direct memory or some form of distributed memory management architecture (e.g., a local or remote caching solution). Additionally, or alternatively, the memory management module 216 deploys multiple different types of memory management architectures and solutions (e.g., reactive caching approaches such as lazy loading or a proactive approach such as write-through cache may be employed). These architectures and solutions are deployed in the form of a flat (single-tiered) cache or a multi-tiered caching architecture where each layer of the caching architecture can be implemented using a different caching technology or architecture solution approach. In such implementations, each cache or caching tier can be configured (e.g., by the configuration 222) independently of the requirements for one or more modules of the overlay system 202. For example, data priority and an eviction strategy, such as least-frequently-used (LFU) or least-recently-used (LRU), can be configured for all or parts of the executable graph-based model 100. In one embodiment, the memory management module 216 is communicatively coupled (e.g., connected either directly or indirectly) to one or more macro-overlays and/or one or more micro-overlays within the executable graph-based model 100.

The storage management module 218 may include suitable logic, circuitry, interfaces, and/or code, executable by the circuitry, configured to manage the temporary or permanent storage of data to facilitate in-situ data processing in the overlay system 202. The storage management module 218 is any suitable low-level storage device solution (such as a file system) or any suitable high-level storage technology such as another database technology (e.g., relational database management system (RDBMS) or NoSQL database). The storage management module 218 is directly connected to the storage device upon which the relevant data is persistently stored. For example, the storage management module 218 can directly address the computer-readable medium (e.g., hard disk drive, external disk drive, or the like) upon which the data is being read or written. Alternatively, the storage management module 218 is connected to the storage device via a network, such as the network 230. As will be described in more detail later in the present disclosure, the storage management module 218 uses 'manifests' to manage the interactions between the storage device and the modules within the overlay system 202. In one embodiment, the storage management module 218 is communicatively coupled (e.g., connected either directly or indirectly) to one or more macro-overlays and/or micro-overlays within the executable graph-based model 100.

As described, storage, loading, and unloading of the executable graph-based model 100 or one or more components thereof may be facilitated by the memory management module 216 and the storage management module 218. The memory management module 216 and the storage management module 218 may facilitate such operations by interacting with the storage device. In the present disclosure, the executable graph-based model 100 may be stored in a storage element. The storage element corresponds to a combination of the memory management module 216 and the storage management module 218 that may be configured to store the executable graph-based model 100. In some embodiments, the storage element may be a storage module that is managed by the memory management module 216 and the storage management module 218, collectively.

The security module 220 may include suitable logic, circuitry, interfaces, and/or code, executable by the circuitry, configured to manage the security of the overlay system 202. This includes security at a system level and a module level. Security is hardware-related, network-related, or software-related, depending on the operational environment, the architecture of the deployment, or the data and information contained within the overlay system 202. For example, if the system is deployed with a web-accessible API (as described above in relation to the interface module 204), the security module 220 can enforce a hypertext transfer protocol secure (HTTPS) protocol with the necessary certification. As a further example, if the data or information associated with the message received or processed by the overlay system 202 contains Personally Identifiable Information (PII) or Protected Health Information (PHI), the security module 220 can implement one or more layers of data protection to ensure that the PII or PHI is correctly processed and stored. In an additional example, in implementations where the overlay system 202 operates on United States of America citizen medical data, the security module 220 may enforce additional protections or policies as defined by the United States Health Insurance Portability and Accountability Act (HIPAA). Similarly, if the overlay system 202 is deployed in the European Union (EU), the security module 220 may enforce additional protections or policies to ensure that the data processed and maintained by the overlay system 202 complies with the General Data Protection Regulation (GDPR). In one embodiment, the security module 220 is communicatively coupled (e.g., connected either directly or indirectly) to one or more macro-overlays and/or one or more micro-overlays within the executable graph-based model 100 thereby directly connecting security execution to the data/information in the executable graph-based model 100.

In addition to the abovementioned components, the overlay system 202 further includes a data management module 234. The data management module 234 may include suitable logic, circuitry, interfaces, and/or code, executable by the circuitry, configured to manage all data or information (e.g., the dataset 226) within the overlay system 202 for a given application. Operations performed by the data management module 234 include data loading, data unloading, data modeling, and data processing. The data management module 234 is communicatively coupled (e.g., connected either directly or indirectly) to one or more other modules within the overlay system 202 to complete some or all of these operations. For example, data storage is handled by the data management module 234 in conjunction with the storage management module 218.

In one embodiment of the present disclosure, the overlay system 202 may further include a templating module 236. The templating module 236 may include suitable logic, circuitry, interfaces, and/or code, executable by the circuitry, configured to implement a templated version of the executable graph-based model 100. The templating module 236 may be further configured to generate specific instances of nodes from predefined templates for the implementation of the templated version of the executable graph-based model 100. In the templated version of the executable graph-based model 100, each node includes a node template and one or more node instances. The node template corresponds to a predefined node structure and each node instance corresponds to an implementation of the corresponding node template The templating module 236 ensures ontology integrity by enforcing the structure and rules of a template when generating instances of the template at run-time. The templating module 236 is communicatively coupled (i.e., connected either directly or indirectly) to one or more nodes within the templated version of the executable graph-based model 100.

In some embodiments, all the modules of the overlay system 202 except for the executable graph-based model 100 may collectively form processing circuitry that executes operations associated with the resource utilization within the overlay system 202.

The functionality of two or more of the modules included in the overlay system 202 may be combined within a single module. Conversely, the functionality of a single module can be split into two or more further modules which can be executed on two or more devices. The modules described above in relation to the overlay system 202 can operate in a parallel, distributed, or networked fashion. The overlay system 202 may be implemented in software, hardware, or a combination of both software and hardware. Examples of suitable hardware modules include a general-purpose processor, a field programmable gate array (FPGA), and/or an application-specific integrated circuit (ASIC). Software modules can be expressed in a variety of software languages such as C, C++, Java, Ruby, Visual Basic, Python, and/or other object-oriented, procedural, or programming languages.

It will be apparent to a person skilled in the art that whilst only one executable graph-based model 100 is shown in FIG. 2, in other embodiments the overlay system 202 stores and maintains more than one executable graph-based model, without deviating from the scope of the present disclosure. In such embodiments, resource utilization associated with each executable graph-based model is in a manner that is similar to that in the executable graph-based model 100.

Having described the overlay system 202 for executing and managing executable graph-based models, the description will now turn to the concept of a node and a node element. Unlike conventional graph-based systems, all elements (e.g., data, overlays, etc.) within the executable graph-based model (e.g., the executable graph-based model 100) are implemented as nodes or node elements. As will become clear, this allows executable graph-based models to be flexible, extensible, and highly configurable.

Figure 3A:
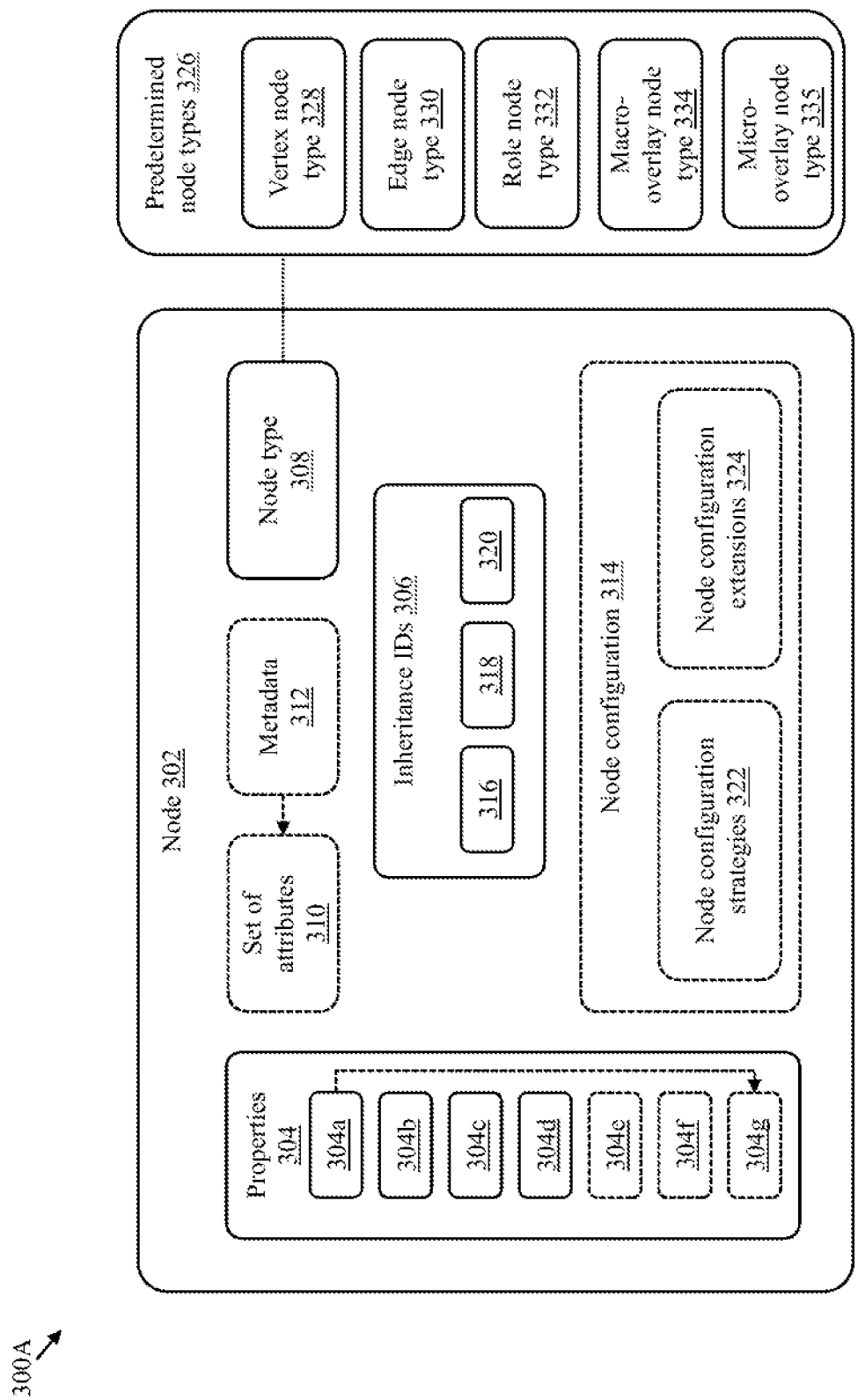
FIG. 3A is a block diagram that illustrates a generic structure of a node within the executable graph-based model, in accordance with an embodiment of the present disclosure.

FIG. 3A is a block diagram 300A that illustrates a generic structure of a node 302 within the executable graph-based model 100, in accordance with an embodiment of the present disclosure. Referring to FIG. 3A, the node 302 corresponds to the core structure of the executable graph-based model 100 and forms the foundational building block for all data and processing logic within the executable graph-based model 100. The node 302 includes properties 304, inheritance IDs 306, and a node type 308. The node 302 optionally includes a set of attributes 310, metadata 312 associated with the attributes 310, and a node configuration 314.

The properties 304 of the node 302 include a unique ID 304a, a version ID 304b, a namespace 304c, and a name 304d. The properties 304 optionally include a set of icons 304e, a set of labels 304f, and one or more alternative IDs 304g. The inheritance IDs 306 of the node 302 include an abstract flag 316, a leaf flag 318, and a root flag 320. The node configuration 314 optionally includes one or more node configuration strategies 322 and one or more node configuration extensions 324. Each of the unique ID 304a, the version ID 304b, the namespace 304c, the name 304d, each of the set of icons 304e, each of the set of labels 304f, each of the set of attributes 310, the metadata 312, the node configuration 314, each of the one or more node configuration strategies 322, and each of the one or more node configuration extensions 324 corresponds to a node element of the node 302. That is to say, the node 302 includes a plurality of node elements that include at least two of a group consisting of the unique ID 304a, the version ID 304b, the namespace 304c, the name 304d, the set of icons 304e, the set of labels 304f, the set of attributes 310, the metadata 312, the node configuration 314, the one or more node configuration strategies 322, and the one or more node configuration extensions 324.

The unique ID 304a is unique for each node within the executable graph-based model 100. The unique ID 304a is used to register, manage, and reference the node 302 within the system (e.g., the overlay system 202). In some embodiments, the one or more alternative IDs 304g are associated with the unique ID 304a to help manage communications and connections with external systems (e.g., during configuration, sending stimuli, or receiving outcomes). The version ID 304b of the node 302 is incremented when the node 302 undergoes transactional change. This allows the historical changes between versions of the node 302 to be tracked by modules or overlays within the overlay system 202. The namespace 304c of the node 302, along with the name 304d of the node 302, is used to help organize nodes within the executable graph-based model 100. That is, the node 302 is assigned a unique name 304d within the namespace 304c such that the name 304d of the node 302 need not be unique within the entire executable graph-based model 100, only within the context of the namespace 304c to which the node 302 is assigned. The node 302 optionally includes one or more icons 304e which are used to provide a visual representation of the node 302 when visualized via a user interface. The one or more icons 304e can include icons at different resolutions and display contexts such that the visualization of the node 302 is adapted to different display settings and contexts. The node 302 also optionally includes one or more labels 304*f* which are used to override the name 304*d* when the node 302 is rendered or visualized.

The node 302 supports the concept of inheritance of data and processing logic associated with any other node of the executable graph-based model 100 that is inherited by the node 302. This allows the behavior and functionality of the node 302 to be extended or derived from the inherited node of the executable graph-based model 100. The inheritance IDs 306 of the node 302 indicate the inheritance-based information, which may be applicable to the node 302. The inheritance IDs 306 comprise a set of Boolean flags which identify the inheritance structure of the node 302. The abstract flag 316 allows the node 302 to support the construct of abstraction. When the abstract flag 316 takes a value 'true', the node 302 is flagged as abstract, that is to say that it cannot be instantiated or created within an executable graph-based model (e.g., the executable graph-based model 100). Thus, in an instance when the node 302 has the abstract flag 316 set to 'true', the node 302 may only form the foundation of other nodes that inherit therefrom. By default, the abstract flag 316 of the node 302 is set to 'false'. The leaf flag 318 is used to indicate whether any other node may inherit from the node 302. If the leaf flag 318 is set to 'true', then no other node may inherit from the node 302 (but unlike an abstract node, a node with the leaf flag 318 set may be instantiated and created within the executable graph-based model 100). The root flag 320 is used to indicate whether the node 302 inherits from any other node. If the root flag 320 is set to 'true', the node 302 does not inherit from any other node. The node 302 is flagged as leaf (e.g., the leaf flag 318 is set to 'true') and/or root (e.g., the root flag 320 is set to 'true'), or neither (e.g., both the leaf flag 318 and the root flag 320 are set to 'false'). It will be apparent to a person skilled in the art that a node cannot be flagged as both abstract and leaf (e.g., the abstract flag 316 cannot be set to 'true' whilst the leaf flag 318 is set to 'true').

The node type 308 of the node 302 is used to extend the functionality of the node 302. All nodes within the executable graph-based model 100 comprise a node type that defines additional data structures and implements additional executable functionality. A node type thus includes data structures and functionality that are common across all nodes that share that node type. The composition of a node with a node type therefore improves extensibility by allowing the generation of specialized node functionalities for specific application areas. Such extensibility is not present in prior art graph-based models. As illustrated in FIG. 3A, the node 302 and the node type 308 are one logical unit that is not separated in the context of an executing system at run-time (e.g., in the context of the execution of an executable graph-based model).

FIG. 3A further shows the plurality of predetermined node types 326 which provides a non-exhaustive list of node types for the node type 308 associated with the node 302. The plurality of predetermined node types 326 include a vertex node type 328, an edge node type 330, and a role node type 332. The vertex node type 328 (also referred to as a data node type or a value node type) includes common data structures and functionality related to the 'things' modeled in the graph (e.g., the data). The edge node type 330 includes common data structures and functionality related to joining two or more nodes. A node having the edge node type 330 may connect two or more nodes, and thus, the edge node type 330 constructs associations and connections between nodes (for example, objects or 'things') within the executable graph-based model 100. The edge node type 330 is not restricted to the number of nodes that can be associated or connected by a node having the edge node type 330. The data structures and functionality of the edge node type 330 thus define a hyper-edge which allows two or more nodes to be connected through a defined set of roles. Further, a node having the edge node type may be associated with a plurality of roles. The plurality of roles may include one or more role nodes and/or one or more role elements. A role element defines a connective relationship between the two or more nodes, and hence, allows an edge node to connect two or more nodes such that the two or more nodes may have more than one relationship therebetween. A role node corresponds to a node with the role node type 332. The role node type 332 defines a connective relationship between two nodes, for example, an edge node and a first vertex node. A node with the role node type 332 may also define a relationship without expressly defining the first vertex node to which the edge node connects. A number of roles (and thus a number of connections) that an edge node type can have been not limited. As a role node is a node, a role node gains the capabilities, functionality, and extensibility of a node. Further, a role node describes a potentially more complex connective relationship than a role element.

The plurality of predetermined node types 326 further includes a macro-overlay node type 334 and a micro-overlay node type 335. As will be described in more detail below, a node with the macro-overlay node type 334 is used to extend the functionality of a node, such as the node 302, to incorporate processing logic. Unlike non-overlay nodes, a macro-overlay node includes processing logic which determines the functionality of the macro-overlay node. The processing logic of a macro-overlay node includes a block of executable code, or instructions, which carries out one or more operations associated with the in-situ data processing in the overlay system 202. The block of executable code is pre-compiled code, code that requires interpretation at run-time, or a combination of both. Different macro-overlay nodes provide different processing logic to realize different functionality.

A node with the micro-overlay node type 335 is used to extend the functionality of a node element, such as a first label of the set of labels 304*f*, to incorporate processing logic. Unlike non-overlay nodes, a micro-overlay node includes processing logic which determines the functionality of the micro-overlay node. The processing logic of a micro-overlay node includes a block of executable code, or instructions, which carries out one or more operations associated with the in-situ data processing in the overlay system 202. The block of executable code is pre-compiled code, code that requires interpretation at run-time, or a combination of both. Different micro-overlay nodes provide different processing logic to realize different functionality.

In the present disclosure, "overlays" and "overlay nodes" are interchangeably used.

The set of attributes 310 corresponds to the data associated with the node 302 (e.g., the data represented by the node 302 within the executable graph-based model 100 as handled by the data management module 234). Notably, a node in the executable graph-based model 100 that is not associated with data may not have any attributes. The set of attributes 310 represents a complex data type. Each attribute of the set of attributes 310 is composed of an attribute behavior. Attribute behavior may be one of a standard attribute behavior, a reference attribute behavior, a derived attribute behavior, and a complex attribute behavior. The attribute behavior of each attribute defines the behavior of the corresponding attribute. The attribute behavior of each attribute may be configured by associated attribute configurations. The attribute configurations are examples of attribute configuration extensions which are node configuration extensions (e.g., they are part of the one or more node configuration extensions 324 of the node 302 shown in FIG. 3A). The standard attribute behavior may be configured by a standard attribute configuration, the reference attribute behavior may be configured by a reference attribute configuration, the derived attribute behavior is configured by a derived attribute configuration, and the complex attribute behavior is configured by a complex attribute configuration.

The attribute behavior defines the behavior of the corresponding attribute. The standard attribute behavior is a behavior that allows read-write access to the data of the corresponding attribute. The reference attribute behavior is a behavior that allows read-write access to the data of the corresponding attribute but restricts possible values of the data to values defined by a reference data set. The reference attribute configuration associated with the reference attribute behavior includes appropriate information to obtain a reference data set of possible values. The derived attribute behavior is a behavior that allows read-only access to data of the corresponding attribute. Also, data of the corresponding attribute is derived from other data or information, within the executable graph-based model 100, in which an executable node of the corresponding attribute is used. The data is derived from one or more other attributes associated with the node or is derived from more complex expressions depending on the application area. In one embodiment, the derived attribute configuration (which is used to configure the derived attribute behavior) includes mathematical and/or other forms of expressions (e.g., regular expressions, templates, or the like) that are used to derive the data (value) of the corresponding attribute. The complex attribute behavior is a behavior that allows the corresponding attribute to act as either a standard attribute behavior if the data of the corresponding attribute is directly set, or a derived attribute behavior if the data of the corresponding attribute is not directly set.

As shown, the node 302 further includes the metadata 312 (e.g., data stored as a name, a count of processed messages, time when the last message was processed, an average processing time required for processing a message, or the like) which is associated with either the node 302 or an attribute (for example, the set of attributes 310) of the node 302.

The node configuration 314 provides a high degree of configurations for the different elements of the node 302. The node configuration 314 optionally includes the one or more node configuration strategies 322 and/or the one or more node configuration extensions 324 which are complex data types. An example of a concrete node configuration strategy is an ID strategy, associated with the configuration of the unique ID 304a of the node 302, which creates message source IDs. A further example of a concrete node configuration strategy is a versioning strategy, associated with the configuration of the version ID 304b of the node 302, which supports major and minor versioning (depending on the type of transactional change incurred by the node 302). The versioning strategy may be adapted to a native filing system of a user device hosting the overlay system 202 or a third-party data storage (for example, Snowflake®, or the like) associated with the overlay system 202.

Figure 3B:
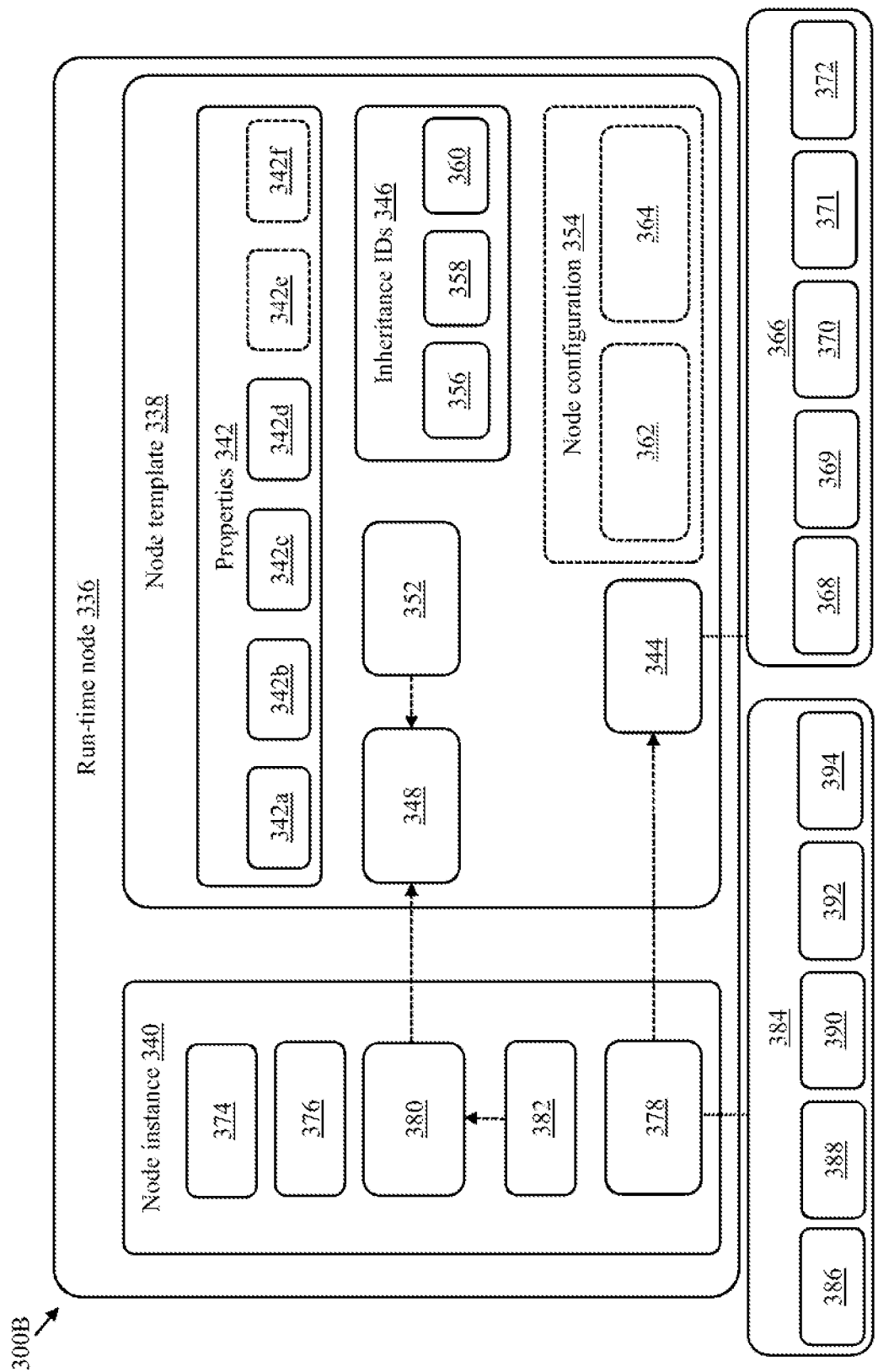
FIG. 3B is a block diagram that illustrates a generic structure of a run-time node within the executable graph-based model, in accordance with an embodiment of the present disclosure.

FIG. 3B is a block diagram 300B that illustrates a generic structure of a run-time node 336 within the executable graph-based model 100, in accordance with an embodiment of the present disclosure. Referring to FIG. 3B, the run-time node 336 corresponds to the core structure of the executable graph-based model 100 and forms the foundational building block for all data and processing logic within the executable graph-based model 100. The run-time node 336 is shown to include a node template 338 and a node instance 340. The node instance 340 is generated according to the node template 338. The node template 338 forms a data structure for the node instance 340. The run-time node 336 shown in FIG. 3B is a compositional structure that is generated and executed, at run-time as part of the executable graph-based model 100. In other words, the node template 338 is defined 'offline' and the node instance 340 and the run-time node 336 are run-time structures that are dynamically generated during execution of the executable graph-based model 100.

The node template 338 comprises a predetermined node structure. Further, the node template 338 defines one or more rules that govern the generation of the node instance 340. The node instance 340 is an implementation of the node template 338. In other words, the node instance 340 is generated based on the predetermined node structure and the one or more rules of the node template 338. The node template 338 cannot be modified during the execution but may be modified during offline mode or at rest. During execution, only the node instance 340 of the run-time node 336 may be modified.

The node template 338 includes properties 342, a node type template 344, inheritance IDs 346, and a set of attribute templates 348. The node template 338 may optionally include metadata 352 and node configuration 354. The properties 342 of the node template 338 include a unique ID 342a, a version ID 342b, a namespace 342c, a name 342d, and optionally include one or more icons 342e and a set of labels 342f. The inheritance IDs 346 comprise an abstract flag 356, a leaf flag 358, and a root flag 360. The node configuration 354 optionally comprises one or more node configuration strategies 362 and/or one or more node configuration extensions 364. FIG. 3B further shows a plurality of predetermined node type templates 366. The plurality of predetermined node type templates 366 include a vertex node type template 368, an edge node type template 369, a role node type template 370, a macro-overlay node template 371, and a micro-overlay node type template 372. Further, the node instance 340 includes a unique ID 374, a version ID 376, a node type instance 378, and a set of attribute instances 380. The node instance 340 may optionally include metadata 382. FIG. 3B further shows a plurality of predetermined node type instances 384. The plurality of predetermined node type instances 384 include a vertex node type instance 386, an edge node type instance 388, a role node type instance 390, a macro-overlay node type instance 392, and a micro-overlay node type instance 394.

Each of the unique ID 342a, the version ID 342b, the namespace 342c, the name 342d, the one or more icons 342e, the set of labels 342f, the set of attribute templates 348, the metadata 352, the node configuration 354, the one or more node configuration strategies 362, the one or more node configuration extensions 364, the unique ID 374, the version ID 376, the set of attribute instances 380, and the metadata 382 corresponds to a node element. That is to say, the run-time node 336 includes the plurality of node elements, where the plurality of node elements includes the unique ID 342a, the version ID 342b, the namespace 342c, the name 342d, the one or more icons 342e, the set of labels 342f, the set of attribute templates 348, the metadata 352, the node configuration 354, the one or more node configuration strategies 362, the one or more node configuration extensions 364, the unique ID 374, the version ID 376, the set of attribute instances 380, and the metadata 382.

The unique ID 342a is unique for each node template within the executable graph-based model 100. Similarly, the unique ID 374 is unique for each node instance within the executable graph-based model 100. The unique ID 342a and the unique ID 374 are used to register, manage, and reference the node template 338 and the node instance 340, respectively, within the overlay system 202. The version ID 342b of the node template 338 is incremented when the node template 338 undergoes transactional change. Similarly, the version ID 376 of the node instance 340 is incremented when the node instance 340 undergoes transactional change. The namespace 342c of the node template 338, along with the name 308d of the node template 338, is used to help organize node templates within the executable graph-based model 100. That is, the node template 338 is assigned a unique name 342d within the namespace 342c such that the name 342d of the node template 338 need not be unique within the entire executable graph-based model 100, only within the context of the namespace 342c to which the node template 338 is assigned. The node template 338 optionally comprises one or more icons 342e which are used to provide a visual representation of the node template 338. The one or more icons 342e can include icons at different resolutions and display contexts such that the visualization of the node is adapted to different display settings and contexts. The node template 338 also optionally comprises the set of labels 342f which are used to override the name 342d when the node template 338 is rendered or visualized.

The node template 338 supports the software development feature of multiple inheritance by maintaining references (not shown) to zero or more other node templates, which then act as the base of the node template 338. This allows the behavior and functionality of a node template to be extended or derived from one or more other node templates within an executable graph-based model (such as the executable graph-based model 100). The node instance 340 likewise supports multiple inheritance because it is an instance representation of the node template 338. The multiple inheritance structure of the node instance 340 is, however, limited to the corresponding instance realization of the multiple inheritance structure defined by the node template 338, i.e., one node instance 340 is created and managed for each node template 338 defined in the inheritance hierarchy for a node instance of a node template.

The inheritance IDs 346 of the node template 338 provide an indication of the inheritance-based information, which is applicable, or can be applicable, to the node template 338. The inheritance IDs 346 has a description that is similar to the inheritance IDs 306. The abstract flag 356 has a description that is similar to the abstract flag 316, the leaf flag 358 has a description that is similar to the leaf flag 318, and the root flag 360 has a description that is similar to the root flag 320.

All elements within the executable graph-based model 100 are defined as node templates or node instances. The functionality of the node template 338 and the node instance 340 are realized due to the use of the node type template 344 and the node type instance 378. The node type template 344 of the node template 338 is used to extend the functionality of the node template 338 by defining the standard set of capabilities, including data and associated behavior. The vertex node type template 368 (also referred to as a data node type) includes a template of common data structures and functionality related to the 'things' modeled in the graph (e.g., the data). The vertex node type instance 386 includes the common data structures and functionality related to the 'things' modeled in the graph based on the vertex node type template 368. The edge node type template 369 includes a template of common data structures and functionality related to joining two or more nodes. A node instance having the edge node type instance 388 may connect two or more nodes and thus the edge node type instance 388 constructs associations and connections between nodes (for example objects or 'things') within the executable graph-based model 100. The edge node type instance 388 is not restricted to the number of nodes that can be associated or connected by a node having the edge node type instance 388. The data structures and functionality of the edge node type instance 388 thus define a hyper-edge which allows two or more nodes to be connected through a defined set of roles. The role node type template 370 includes a template of common data structures and functionality related to defining a connective relationship between the two or more nodes, and hence, allows an edge node to connect two or more nodes such that the two or more nodes may have more than one relationship therebetween. A node instance having the role node type instance 390 defines the connective relationship between two or more nodes.

The macro-overlay node type template 371 is used to extend the functionality of a node template (e.g., the node template 338) to incorporate processing logic. Similarly, the macro-overlay node type instance 392 is used to extend the functionality of a node instance (e.g., the node instance 340) to incorporate processing logic. The micro-overlay node type template 372 is used to extend the functionality of a node element of the node template (e.g., the node template 338) to incorporate processing logic. Similarly, the micro-overlay node type instance 394 is used to extend the functionality of a node element of a node instance (e.g., the node instance 340) to incorporate processing logic.

The set of attribute templates 348 corresponds to the data defined by the node template 338. For example, the set of attribute templates 348 may define the names and value types (e.g., integer, string, float, etc.) of one or more attributes but not the values of these attributes. The values of the set of attribute templates 348 may be defined by the set of attribute instances 380 of the node instance 340 through one or more values or instance values. For example, the node template 338 may define a string attribute 'surname' and the corresponding node instance 340 may assign the instance value 'Bell-Richards' to this string attribute. Each attribute instance of the set of attribute instances 380 is associated with an attribute template of the set of attribute templates 348. The node template 338 may define one or more default values for the set of attribute templates 348. The default values correspond to the values that the attributes take if no value is assigned. The metadata 352 (e.g., data stored as a name, value type, and value triplet) is associated with either the node template 338 or one or more of the set of attribute templates 348 of the node template 338. Similarly, the node instance 340 also optionally comprises the metadata 352 (e.g., data stored as a name, value type, and value triplet) which is associated with either the node instance 340 or one or more of the set of attribute instances 380.

The node configuration 354 provides a high degree of configurability for the different elements of a node template and/or node instance. An example of a concrete node configuration strategy is an ID strategy, associated with the configuration of the unique ID 342a of the node template 338. A further example of a concrete node configuration strategy is a versioning strategy, associated with the configuration of the version ID 342b of the node template 338 which supports major and minor versioning (depending on the type of transactional change incurred). The versioning strategy may be adapted to a native filing system of a user device hosting the overlay system 202 or a third-party data storage (for example, Snowflake®, or the like) associated with the overlay system 202.

Although it is provided that the node template 338 is associated with one node instance (e.g., the node instance 340), the scope of the present disclosure is not limited to it. In other embodiments, the node template 338 may be further associated with two or more node instances where the two or more node instances correspond to two or more implementations of the node template 338, respectively.

Figure 4A:
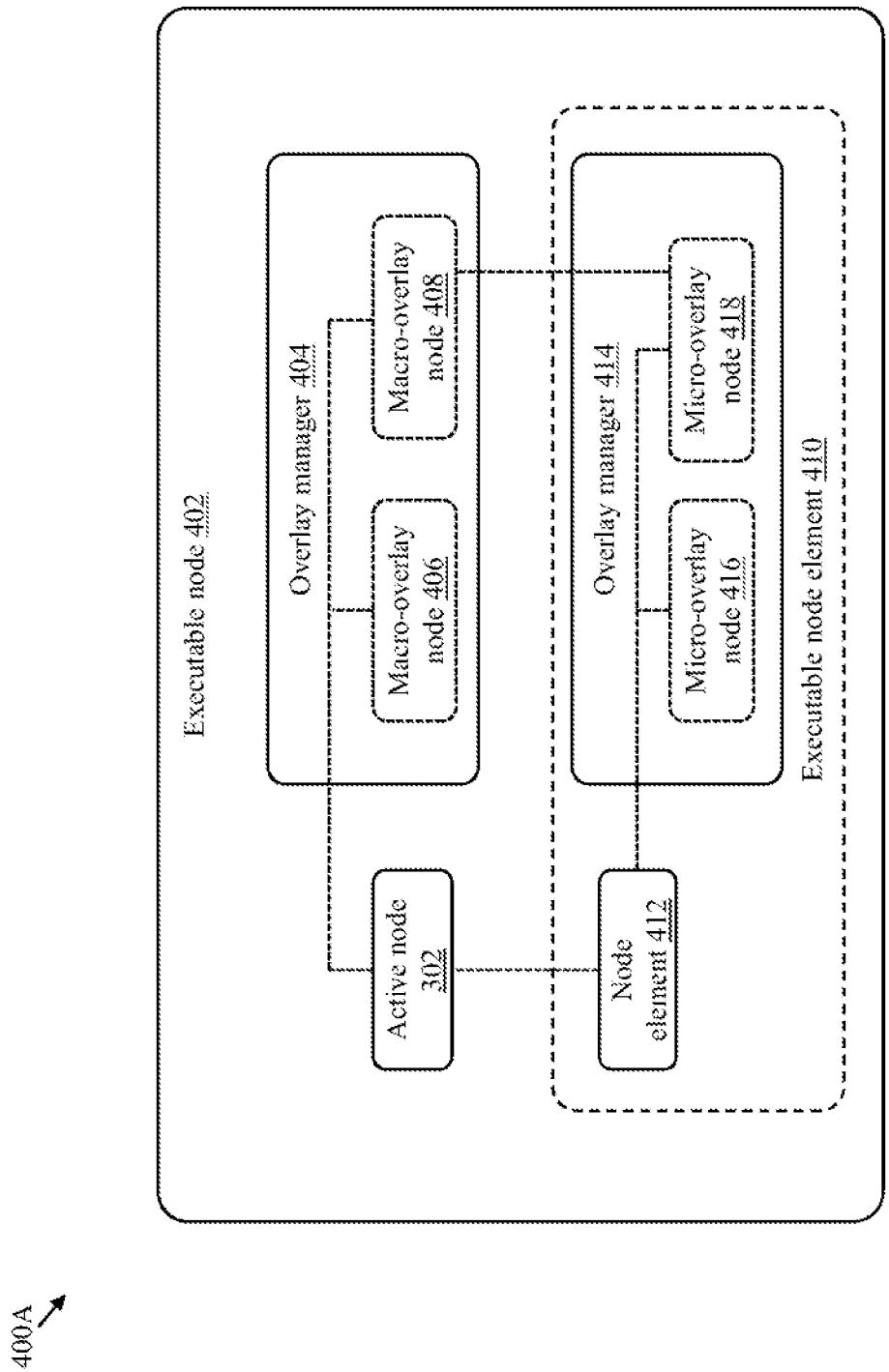
FIG. 4A is a block diagram that illustrates an executable node within the executable graph-based model, in accordance with an embodiment of the present disclosure.

FIG. 4A is a block diagram 400A that illustrates an executable node 402 within the executable graph-based model 100, in accordance with an embodiment of the present disclosure. Referring to FIG. 4A, the executable node 402 is shown to include an active node (e.g., the node 302 or the run-time node 336) and an overlay manager 404. For the sake of ongoing discussion, the active node corresponds to the node 302, and is hereinafter referred to as the "active node 302". However, the functionality of the executable node 402 for the active node corresponding to the node 302 may be similar to that for the active node corresponding to the run-time node 336.

The overlay manager 404 includes a macro-overlay node 406 and a macro-overlay node 408. The executable node 402 provides processing functionality (e.g., processing logic) to the active node 302 via one or more associated macro-overlay nodes (for example, the macro-overlay nodes 406 and 408). Beneficially, the data and processing capability of the active node 302 may be dynamically and significantly extended using the concept of an executable node (for example, the executable node 402).

The executable node 402 is further shown to include an executable node element 410. In other words, the active node 302 includes the executable node element 410. The executable node element 410 includes a node element 412 and an overlay manager 414. The node element 412 corresponds to one of the plurality of node elements described in FIG. 3A. For the sake of ongoing discussion, the node element 412 is assumed to be one of the set of attributes 310. The overlay manager 414 includes a micro-overlay node 416 and a micro-overlay node 418. The micro-overlay nodes 416 and 418 provide processing functionality (e.g., processing logic) to the node element 412. That is to say, a data element with one or more micro-overlay nodes forms an executable node element. Beneficially, the data and processing capability of the node element 412 may be dynamically and significantly extended using the concept of an executable node element (for example, the executable node element 410). Each of the micro-overlay nodes 416 and 418 can be executed only for the node element 412. That is to say, each of the micro-overlay nodes 416 and 418 is capable of extending the functionality of the node element 412. On the other hand, each of the macro-overlay nodes 406 and 408 is capable of extending the functionality of the active node 302. Each of the micro-overlay nodes 416 and 418 is not capable of extending the functionality of the active node 302. Further, when the active node 302 has the edge node type 330, each of the macro-overlay nodes 406 and 408 may extend the functionality of one or more nodes that are coupled to the active node 302.

Each of the macro-overlay nodes 406 and 408 and the micro-overlay nodes 416 and 418 have an overlay node type. Examples of an overlay node type include an encryption overlay node type, an audit overlay node type, an obfuscation overlay node type, a history overlay node type, a location overlay node type, a data quality overlay node type, or the like. Each macro-overlay node and micro-overlay node, being a node, adheres to the generic structure of a node described in conjunction with FIG. 3A.

Macro-overlay nodes and micro-overlay nodes with an encryption overlay node type are nodes that include processing logic for encrypting the corresponding executable node and executable data element, respectively. Macro-overlay nodes and micro-overlay nodes with an obfuscating overlay node type are nodes that include processing logic for obfuscating the corresponding executable node and executable data element, respectively. Macro-overlay nodes and micro-overlay nodes with an audit overlay node type are nodes that include processing logic for maintaining a record of any changes to the corresponding executable node and executable data element, respectively. Macro-overlay nodes and micro-overlay nodes with a history overlay node type are nodes that include processing logic for facilitating creation, maintenance, and utilization of history associated with the corresponding executable node and executable data element, respectively. Macro-overlay nodes and micro-overlay nodes with a location overlay node type are nodes that include processing logic for holding storage location information where the corresponding executable node and executable data element, respectively, are to be persisted. Macro-overlay nodes and micro-overlay nodes with a data quality overlay node type are nodes that include processing logic for determining the quality value of data/information stored in the corresponding executable node and executable data element, respectively.

The executable node 402 extends the active node 302 (or is a subtype of the active node 302) such that all the functionality and properties of the active node 302 are accessible to the executable node 402. The executable node 402 also dynamically extends the functionality of the active node 302 by associating the macro-overlay nodes maintained by the overlay manager 404 with the active node 302. The executable node 402 may thus be considered a composition of the active node 302, the macro-overlay node 406, and the macro-overlay node 408. The executable node 402 may be alternatively referred to as a node with overlay. Therefore, the executable node 402 acts as a decorator of the active node 302 adding the functionality of the overlay manager 404 to the active node 302.

Although, the executable node 402 is shown to include two macro-overlay nodes (e.g., the macro-overlay nodes 406 and 408), in other embodiments, the executable node 402 may include any number of macro-overlay nodes, without deviating from the scope of the present disclosure.

The executable node element 410 extends the node element 412 such that all the functionality and properties of the node element 412 are accessible to the executable node element 410. The executable node element 410 also dynamically extends the functionality of the node element 412 by associating the micro-overlay nodes maintained by the overlay manager 414 with the node element 412. The executable node element 410 may thus be considered a composition of the node element 412, the micro-overlay node 416, and the micro-overlay node 418. The executable node element 410 may be alternatively referred to as a node element with overlay. Therefore, the executable node element 410 acts as a decorator of the node element 412 adding the functionality of the overlay manager 414 to the node element 412.

Although, the executable node element 410 is shown to include two micro-overlay nodes (e.g., the micro-overlay nodes 416 and 418), in other embodiments, the executable node 402 may include any number of micro-overlay nodes, without deviating from the scope of the present disclosure.

It will be apparent to a person skilled in the art that the active node 302 refers to any suitable node within the executable graph-based model 100. As such, the active node 302 may be a node having a type such as a vertex node type, an edge node type, a role node type, or the like.

The overlay manager 404 registers and maintains one or more macro-overlay nodes (such as the macro-overlay nodes 406 and 408) associated with the active node 302. The assignment of the macro-overlay node 406 to the active node 302 (via the overlay manager 404) endows the active node 302 with processing logic and executable functionality defined within the macro-overlay node 406. Similarly, the assignment of the macro-overlay node 408 to the active node 302 (via the overlay manager 404) endows the active node 302 with processing logic and executable functionality defined within the macro-overlay node 408. Similarly, the overlay manager 414 registers and maintains one or more micro-overlay nodes (such as the micro-overlay nodes 416 and 418) associated with the node element 412. The assignment of the micro-overlay node 416 to the node element 412 (via the overlay manager 414) endows the node element 412 with processing logic and executable functionality defined within the micro-overlay node 416. Similarly, the assignment of the micro-overlay node 418 to the node element 412 (via the overlay manager 414) endows the node element 412 with processing logic and executable functionality defined within the micro-overlay node 418.

Extending the functionality of (i) an active node through one or more macro-overlay nodes and (ii) a node element through one or more micro-overlay nodes, is at the heart of the overlay system 202. As illustrated in FIG. 3A, the data (e.g., a vertex node as represented by the active node 302 and/or the node element 412) and the functionality that acts upon that data (e.g., a macro-overlay node and/or a micro-overlay node) can be separated and independently maintained offline, but at run-time, an association between the data node/node element and the macro-overlay node/micro-overlay node is determined and an executable node/executable node element is generated (e.g., the executable node 402/the executable node element 410, shown in FIG. 4A).

An overlay node such as a macro-overlay node and/or a micro-overlay node, is not bound to a single executable node or a single executable graph-based model (unlike nodes that have non-overlay node types). This allows overlay nodes to be centrally managed and reused across multiple instances of executable graph-based models. Notably, a node (for example, a data node, an executable node, and an overlay node) may be extended by way of overlays. Further, each overlay node may be extended to have one or more macro-overlays and/or micro-overlays. Such overlays may be termed chaining overlays.

Unlike non-overlay nodes, an overlay node such as a macro-overlay node and/or a micro-overlay node includes processing logic (not shown in FIG. 4) which determines the functionality of the overlay node. The processing logic of an overlay node includes executable code, or instructions, which carries out one or more operations associated with facilitating resource utilization within the overlay system 202. The executable code may be pre-compiled code, code that requires interpretation at run-time, or a combination of both. Different overlay nodes provide different processing logic to realize different functionality.

Although it is illustrated that the active node 302 includes one executable node element 410, the scope of the present disclosure is not limited to it. In other embodiments, the active node 302 may include more than one executable node element. That is to say, more than one node element of the plurality of node elements may correspond to an executable node element.

In an embodiment, the macro-overlay node 408 is configured to store association data that is indicative of an association of the micro-overlay node 418 with the node element 412. Thus, FIG. 4A illustrates an association between the macro-overlay node 408 and the micro-overlay node 418. That is to say, the macro-overlay node 408 is aware of the association of the micro-overlay node 418 with the node element 412. The association data may be utilized during the execution of the macro-overlay node 408.

Figure 4B:
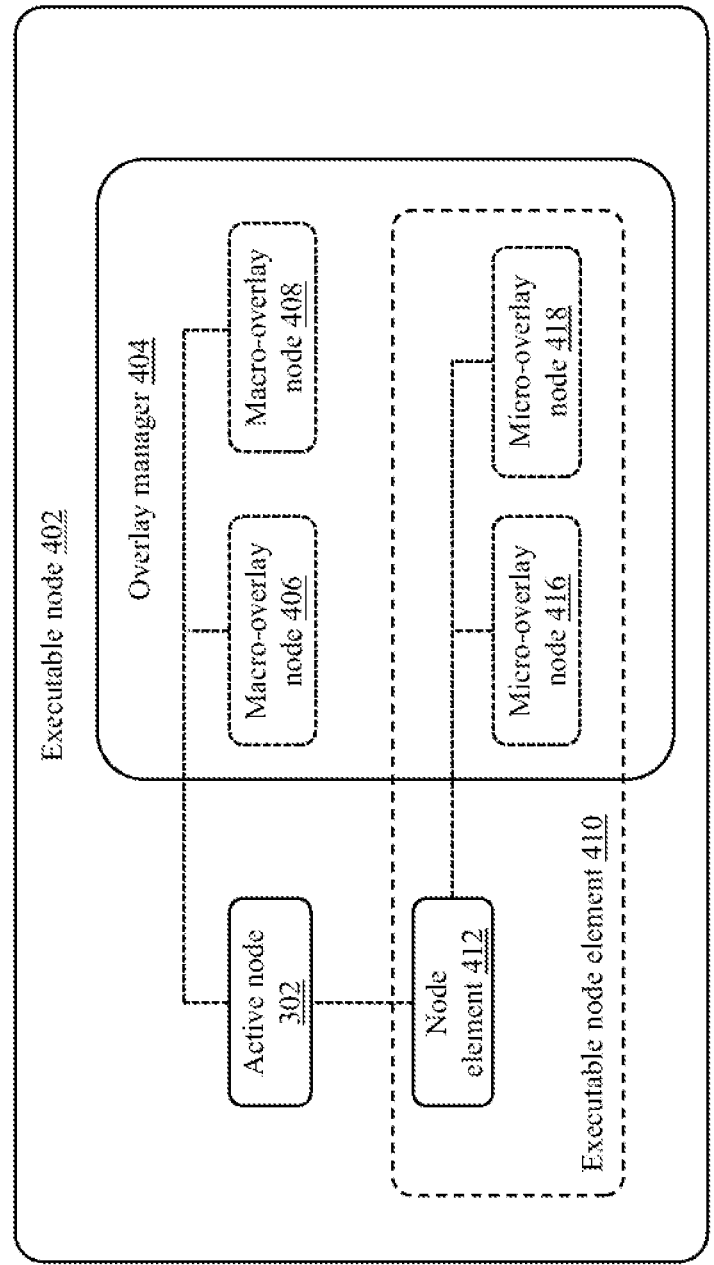
FIG. 4B is a block diagram that illustrates an executable node within the executable graph-based model, in accordance with another embodiment of the present disclosure.

FIG. 4B is a block diagram 400B that illustrates the executable node 402 within the executable graph-based model 100, in accordance with another embodiment of the present disclosure. FIG. 4B is similar to FIG. 4A except for the overlay manager 404 of the executable node 402 including the micro-overlay nodes 416 and 418 associated with the executable node element 410. That is to say, the micro-overlay nodes 416 and 418 associated with the node element 412 are maintained by the overlay manager 404. Thus, the node element 412 may interact with the overlay manager 404 to identify the micro-overlay nodes 416 and 418 for executing a corresponding operation.

The maintenance of the micro-overlay nodes 416 and 418 by the overlay manager 404 proves to be beneficial when the micro-overlay nodes 416 and 418 are to be utilized for extending functionalities of more than one node element of the active node 302. That is to say, when the micro-overlay nodes 416 and 418 are maintained by the overlay manager 404, the micro-overlay nodes 416 and 418 can extend the functionality of two or more node elements of the active node 302 without a need for each of the two or more node elements being associated with a dedicated overlay manager that stores micro-overlay nodes associated therewith.

In an embodiment, the micro-overlay node 416 may be maintained by the overlay manager 404 and the micro-overlay node 418 may be maintained by the overlay manager 414. Such an arrangement is beneficial when the micro-overlay node 416 is utilized by more than one node element of the active node 302 and the micro-overlay node 418 is utilized only by the node element 412.

The data and the processing logic associated with one or more macro-overlays and/or micro-overlays of an executable node (for example, the executable node 402) are persistent. The persistent nature of the data and the processing logic are described in detail in conjunction with FIG. 5.

Figure 5:
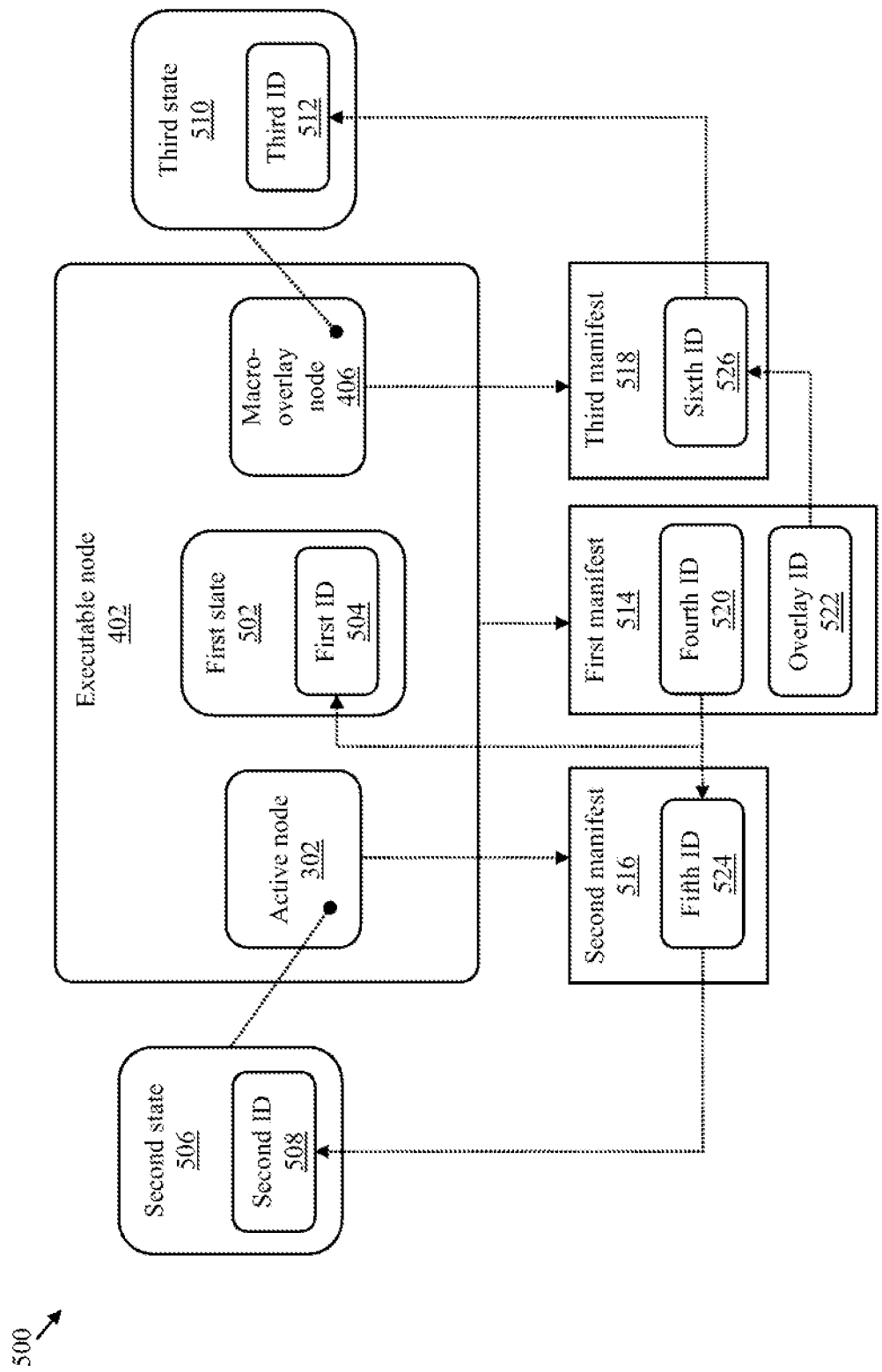
FIG. 5 is a block diagram that illustrates a composition of the executable node that enables persistent storage of data and the processing logic associated therewith, in accordance with an embodiment of the present disclosure.

FIG. 5 is a block diagram 500 that illustrates a composition of the executable node 402 that enables persistent storage of data and the processing logic associated therewith, in accordance with an embodiment of the present disclosure.

As described in conjunction with FIG. 4A, the executable node 402 includes the active node 302 and one or more overlay nodes (e.g., the macro-overlay nodes 406 and 408 and the micro-overlay nodes 416 and 418). For the brevity of the ongoing description, the persistent storage is explained for the executable node 402 including only the macro-overlay node 406. One or more operations performed for ensuring the persistence of the macro-overlay node 406 may be performed for the macro-overlay node 408 and the micro-overlay nodes 416 and 418 as well.

The executable node 402 has a first state 502 having a first ID 504. The active node 302 has a second state 506 having a second ID 508, and the macro-overlay node 406 has a third state 510 having a third ID 512. A manifest (for example, first through third manifests 514-518) is generated for each of the active node 302, the executable node 402, and the macro-overlay node 406. In an embodiment, the manifests may be generated by the storage management module 218. The first manifest 514 is associated with the executable node 402 and has a fourth ID 520 and an overlay ID 522. The second manifest 516 is associated with the active node 302 and has a fifth ID 524. The third manifest 518 is associated with the macro-overlay node 406 and has a sixth ID 526. The second manifest 516 may further include a manifest generated for each node element of the plurality of node elements associated with the active node 302. Further, the manifests are stored at respective storage locations that may be centralized or distributed storage locations associated with the overlay system 202. The manifests may be stored by the storage management module 218.

The first state 502 of the executable node 402 includes data required to reconstruct the executable node 402 (e.g., attributes, properties, etc.). The first state 502 of the executable node 402 is persistently stored along with the first ID 504. The first manifest 514 is generated for the executable node 402 and has (i) the fourth ID 520, (ii) the storage location of the first state 502 of the executable node 402, and (iii) the overlay ID 522. Notably, the fourth ID 520 is the same as the first ID 504 and the fifth ID 524, hence, the first manifest 514 includes the ID of the state of the active node 302 and the executable node 402. Further, the overlay ID 522 is the same as the sixth ID 526 of the state of the macro-overlay node 406. Therefore, the first manifest 514 may be used to identify and retrieve the states of the active node 302, the executable node 402, and the macro-overlay node 406. Subsequently, the retrieved states may be used to reconstruct the executable node 402 and the macro-overlay node 406. In an instance, the executable node 402 may be further extended to include additional overlay nodes. In such an instance, the first manifest 514 may include state IDs of the additional overlay nodes as well. A first manifest state (not shown) is then generated for the first manifest 514 and persistently stored along with the fourth ID 520.

The second state 506 of the active node 302 includes data required to reconstruct the active node 302 (e.g., attributes, properties, etc.) and is persistently stored along with the second ID 508. The second manifest 516 is generated for the active node 302 and has (i) the fifth ID 524 and (ii) the storage location of the second state 506 of the active node 302. The second ID 508 of the second state 506 and the fifth ID 524 of the second manifest 516 are the same as the first ID 504 of the first state 502 of the executable node 402 (which is also the same as the fourth ID 520 of the first manifest 514 of the executable node 402). As mentioned above, along with the first state 502, the first manifest 514 may also be used to identify and retrieve the second manifest 516 which in turn may be used to identify the second state 506 of the active node 302. A second manifest state (not shown) is then generated for the second manifest 516 and persistently stored along with the fifth ID 524. Thus, the states, manifests, and manifest states for the executable node 402 and the active node 302 include the same, shared, ID. A shared ID can be used in this instance because the states, manifests, and manifest states are stored separately. The separate storage of the states, manifests, and manifest states exhibit a distributed architecture of the overlay system 202.

The third state 510 of the macro-overlay node 406 includes data required to reconstruct the macro-overlay node 406 (e.g., attributes, properties, processing logic, etc.) and is persistently stored along with the third ID 512. The third manifest 518 is generated for the macro-overlay node 406 and includes the sixth ID 526, which is the same as the third ID 512. Therefore, the first manifest 514 may be further used to identify and retrieve the third manifest 518 which in turn may be used to identify and retrieve the third state 510 of the macro-overlay node 406. A third manifest state (not shown) is then generated for the third manifest 518 and is persistently stored along with the sixth ID 526.

In operation, when the executable node 402 is to be loaded, the transaction module 208, in conjunction with the storage management module 218, may execute one or more operations to retrieve the first manifest state stored at a known storage location. Based on the first manifest state, the storage management module 218 may re-construct the first manifest 514 which includes the fourth ID 520 which is the same as the fifth ID 524 of the second manifest 516. Based on the fifth ID 524, the storage management module 218 may identify the second manifest state and may generate the second manifest 516 based on which the second state 506 is identified. Subsequently, the active node 302 is loaded and the storage management module 218 may determine that the active node 302 is a node with overlay. Based on the fourth ID 520 (that is the same as the first ID 504 of the first state 502 of the executable node 402) of the first manifest 514, the first state 502 is identified and retrieved. Subsequently, the executable node 402 is loaded. Moreover, based on the overlay ID 522 (that is the same as the sixth ID 526 of the third manifest 518) of the first manifest 514, the third manifest state is identified and the third manifest 518 is generated. Subsequently, based on the sixth ID 526 (that is the same as the third ID of the third state) of the third manifest 518, the third state 510 is identified and retrieved. Based on the third state 510, the macro-overlay node 406 is reconstructed and loaded in the executable graph-based model 100.

In some embodiments, the macro-overlay node 406 may not be loaded in case it is not required for executing the operation associated with the set of stimuli 228. The loaded executable node 402 and the macro-overlay node 406 may be unloaded in case they remain unused for a first predefined time period, whereas one or more executable nodes that are used at least once during the first predefined time period may remain loaded in the executable graph-based model 100. In some embodiments, the data and processing logic associated with a loaded executable node and/or overlay node may be transferred to a local memory of the overlay system 202, if the data and the processing logic remain unused for a second predefined time period. Further, the data and the processing logic associated with the executable node/overlay node are transferred to an external storage from the local memory in case the executable node/overlay node remains unused for a third predefined time period. The third predefined time period is greater than the second predefined time period and the second predefined time period is greater than the first predefined time period. The term unloading refers to storing a state of a node with a current version of data and processing logic associated therewith at a storage location that is pointed by the corresponding manifest.

An executable graph-based model (for example, the executable graph-based model 100) may be stored (and loaded) using the above-described composition. Beneficially, each component is stored separately thereby allowing a user to maintain and store their data independently of the storage of the structure and functionality of the executable graph-based model 100.

Notably, all manifest states are stored together at a storage location that is known to the storage management module 218. Such centralized storage of the manifest states ensures that node states associated therewith are easily accessible.

Although FIG. 5 illustrates only a single macro-overlay node, in other embodiments, the executable node 402 may include additional or different macro-overlay nodes and micro-overlay nodes. When the executable node 402 includes micro-overlay nodes (such as the micro-overlay nodes 416 and 418), manifests may be generated for such micro-overlay nodes. Each of the manifests generated for the micro-overlay nodes 416 and 418 may be indicative of the node element 412 that is associated with the micro-overlay nodes 416 and 418. Additionally, each of the manifests generated for the micro-overlay nodes 416 and 418 may be further indicative of the overlay manager that maintains the same. Further, only those macro-overlay nodes and micro-overlay nodes that are required for responding to the set of stimuli 228 may be loaded. The overlay system 202 described above may be used to implement systems and methods for in-situ data processing in the overlay system 202.

Figure 6A:
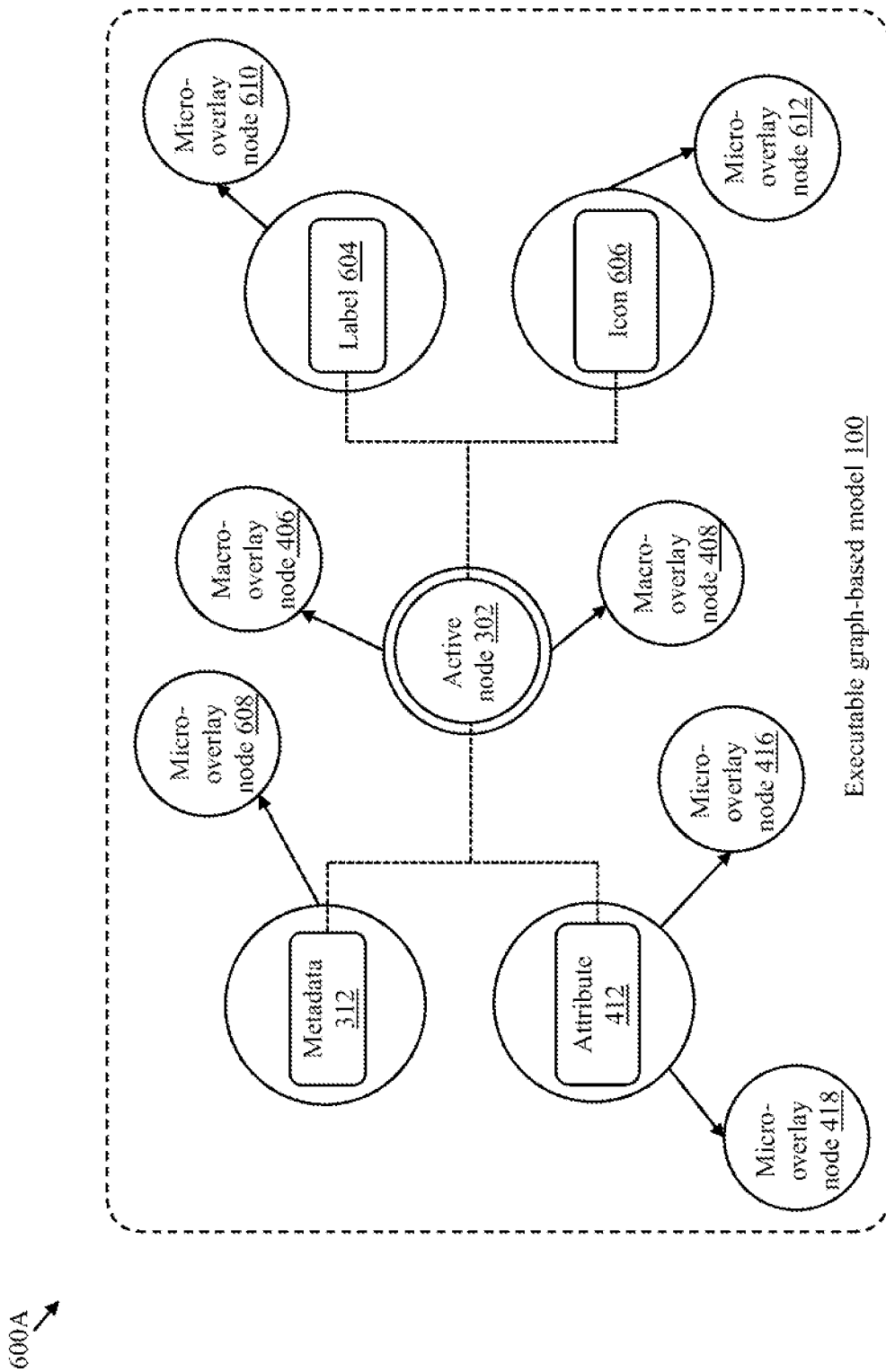
FIG. 6A is a schematic diagram that illustrates in-situ data processing in the overlay system using micro-overlays, in accordance with an embodiment of the present disclosure.

FIG. 6A is a schematic diagram 600A that illustrates in-situ data processing in the overlay system 202 using micro-overlays, in accordance with an embodiment of the present disclosure. Referring to FIG. 6A, the executable graph-based model 100 is shown to include the active node 302. As described in conjunction with FIG. 3A, the active node 302 includes the plurality of node elements. The plurality of node elements includes the node element 412. It is assumed that the node element 412 corresponds to an attribute of the set of attributes 310, and is hereinafter referred to as "the attribute 412". The plurality of node elements may further include the metadata 312, a label 604 of the set of labels 304*f*, and an icon 606 of the set of icons 304*e*. Further, the active node 302 is associated with the macro-overlay nodes 406 and 408, the micro-overlay nodes 416 and 418 are associated with the attribute 412, a micro-overlay node 608 is associated with the metadata 312, a micro-overlay node 610 is associated with the label 604, and a micro-overlay node 612 is associated with the icon 606. The macro-overlay nodes 406 and 408 extend the functionality of the active node 302 and the micro-overlay nodes 416 and 418, 608, 610, and 612 extend the functionality of the attribute 412, the metadata 312, the label 604, and the icon 606, respectively. The active node 302 may correspond to a vertex node, an edge node, a role node, a micro-overlay node, or a macro-overlay node. The processing logic associated with each of the micro-overlay nodes 416, 418, 608, 610, and 612 and the macro-overlay node 406 may be different from each other. That is to say, each of the micro-overlay nodes 416, 418, 608, 610, and 612 and the macro-overlay node 406 may execute different operations.

In operation, the stimuli management module 212 may be configured to receive a first stimulus of the set of stimuli 228. The first stimulus may correspond to a command or a query. Further, the stimuli management module 212, in conjunction with the context module 210 and the controller module 206, may be configured to identify, in the executable graph-based model 100, the active node 302 based on a first context of the first stimulus. Based on the first context of the first stimulus, the stimuli management module 212, in conjunction with the context module 210, the controller module 206, and the overlay management module 214, may be further configured to identify a first set of node elements from the plurality of node elements of the active node 302 and one or more micro-overlay nodes associated with each identified node element, that are required for the processing of the first stimulus. For the sake of ongoing discussion, it is assumed that the first set of node elements includes the attribute 412, the metadata 312, the label 604, and the icon 606. Further, the controller module 206, in conjunction with, the overlay management module 214, may be configured to execute an operation associated with the first stimulus based on the identified first set of node elements and the identified one or more micro-overlay nodes associated with each identified node element. That is to say, the operation associated with the first stimulus is executed based on the attribute 412 and the micro-overlay nodes 416 and 418. Similarly, the operation associated with the first stimulus is executed based on the metadata 312, the label 604, the icon 606, and the micro-overlay nodes 608, 610, and 612. Thus, the present disclosure enables the association of desired processing logic (e.g., processing logic associated with the micro-overlay nodes 416 and 418) to a desired node element (e.g., the attribute 412) instead of associating the processing logic (e.g., the processing logic associated with the micro-overlay nodes 416 and 418) that is desired to be associated with the desired node element with an entire active node (e.g., the active node 302). Thus, the flexibility of the overlay system 202 is improved.

In an embodiment, the stimuli management module 212, in conjunction with, the context module 210, the controller module 206, and the overlay management module 214, may be further configured to identify, for the processing of the first stimulus, one or more macro-overlay nodes from a set of macro-overlay nodes associated with the active node 302, that are required for processing the first stimulus. For example, the macro-overlay node 406 associated with the active node 302 is identified. The controller module 206, in conjunction with the overlay management module 214, may execute the operation associated with the first stimulus further based on the active node 302 and the macro-overlay node 406. In one embodiment, the macro-overlay node 406 associated with the active node 302, is executed prior to the execution of the micro-overlay node associated with each identified node element of the first set of node elements. That is to say, the macro-overlay node 406 associated with the active node 302, is executed prior to the execution of the micro-overlay nodes 416, 418, 608, 610, and 612. In another embodiment, the macro-overlay node 406, associated with the active node 302, is executed after the execution of the micro-overlay node associated with each identified node element of the first set of node elements. That is to say, the macro-overlay node 406 associated with the active node 302, is executed after the execution of the micro-overlay nodes 416, 418, 608, 610, and 612.

The plurality of node elements of the active node 302 may further include a second set of node elements (not shown). The second set of node elements includes each node element of the active node 302 that is described in conjunction with FIG. 3A and not illustrated in FIG. 6A. Each of the second set of node elements may not be associated with a micro-overlay node. Thus, during the execution of the operation associated with the first stimulus, for each node element of the first set of node elements, the corresponding micro-overlay node is executed, whereas, for each node element of the second set of node elements, the macro-overlay node 406 associated with the active node 302 is executed.

During the execution of the operation associated with the first stimulus (i.e., after the reception of the first stimulus and the identification of the active node 302), the determination for which node element of the plurality of node elements, a micro-overlay node is to be executed and for which node element of the plurality of node elements, a macro-overlay node is to be executed may be implemented in multiple ways.

In an embodiment, during the execution of the operation associated with the first stimulus (i.e., after the identification of the active node 302 and the macro-overlay node 406 based on the first context of the first stimulus), the controller module 206, in conjunction with the overlay management module 214, may be further configured to determine, for each node element of the plurality of node elements, whether the corresponding node element is associated with at least one micro-overlay node. For example, the controller module 206, in conjunction with the overlay management module 214, may determine that each of the first set of node elements, that includes the attribute 412, the metadata 312, the label 604, and the icon 606, is associated with one micro-overlay node. Consequently, it is implied that each node element of the second set of node elements is not associated with a micro-overlay node. Thus, the macro-overlay node 406 associated with the active node 302 is executed for each node element of the second set of node elements based on an absence of association of a micro-overlay node with the corresponding node element. Additionally, as each of the first set of node elements is associated with a micro-overlay node, the associated micro-overlay node is executed for the corresponding node element of the first set of node elements.

In another embodiment, the macro-overlay node 406 associated with the active node 302 may be configured to store association data that is indicative of the association of a micro-overlay node with each of the first set of node elements. For example, the macro-overlay node 406 stores association data that is indicative of association of the micro-overlay nodes 416 and 418 with the attribute 412, association of the micro-overlay node 608 with the metadata 312, association of the micro-overlay node 610 with the label 604, and association of the micro-overlay node 612 with the icon 606. Further, during the execution of the operation associated with the first stimulus (i.e., after the identification of the active node 302 and the macro-overlay node 406 based on the first context of the first stimulus), the macro-overlay node 406 may be executed for each node element of the second set of node elements based on an absence of association of a micro-overlay node with the corresponding node element.

Although each of the attribute 412, the metadata 312, the label 604, and the icon 606 is associated with one micro-overlay node, the scope of the present disclosure is not limited to it. In other embodiments, each of the attribute 412, the metadata 312, the label 604, and the icon 606 may be associated with more than one micro-overlay node. That is to say, each of the first set of node elements may be associated with one or more micro-overlay nodes. Additionally, as each of the first set of node elements is associated with a micro-overlay node, the associated micro-overlay node is executed for the corresponding node element of the first set of node elements.

Although it is described that four node elements of the active node 302 are associated with micro-overlay nodes, the scope of the present disclosure is not limited to it. In other embodiments, more than four or less than four node elements of the active node 302 may be associated with one or more micro-overlay nodes.

Although each of the attribute 412, the metadata 312, the label 604, and the icon 606 is associated with different micro-overlay nodes, the scope of the present disclosure is not limited to it. In other embodiments, the attribute 412, the metadata 312, the label 604, and the icon 606 may be associated with a single micro-overlay node. That is to say, the attribute 412, the metadata 312, the label 604, and the icon 606 may share the same micro-overlay node.

Although the executable graph-based model 100 is shown to include one active node 302 with one macro-overlay node 406 associated therewith, the scope of the present disclosure is not limited to it. In other embodiments, the executable graph-based model 100 may include a plurality of active nodes and a plurality of macro-overlay nodes, where each active node, of the plurality of active nodes, is associated with a set of macro-overlay nodes of the plurality of macro-overlay nodes, such that each macro-overlay node, of the set of macro-overlay nodes, is configured to extend the functionality of the corresponding active node. In such an embodiment, each active node of the plurality of active nodes includes a plurality of node elements. Further, the executable graph-based model includes a set of micro-overlay nodes associated with each active node of the plurality of active nodes, such that each micro-overlay node is associated with at least one node element, of the plurality of node elements, and is configured to extend functionality of the corresponding node element. Thus, the first set of node elements identified based on the first context of the first stimulus may further include one or more node elements associated with one or more active nodes. In such an embodiment, at least one micro-overlay node, of the plurality of micro-overlay nodes, may be derived from one or more remaining micro-overlay nodes of the plurality of micro-overlay nodes. Similarly, at least one macro-overlay node, of the plurality of macro-overlay nodes, may be derived from one or more remaining macro-overlay nodes of the plurality of macro-overlay nodes.

In reference to the above-described embodiment, a first set of macro-overlay nodes is associated with the active node 302 where the active node 302 and the first set of macro-overlay nodes associated therewith constitute an executable active node (such as the executable node 402). Similarly, each node element, of the first set of node elements, and at least one micro-overlay node associated therewith constitute an executable node element (such as the executable node element 410). In such a scenario, the executable active node is configured to maintain the first set of macro-overlay nodes, in the executable graph-based model 100. That is to say, the overlay manager 404 of the active node 302 maintains the first set of macro-overlay nodes in the executable graph-based model 100. In one embodiment, the executable active node is further configured to maintain a first set of micro-overlay nodes associated with the active node 302, in the executable graph-based model 100. That is to say, the overlay manager 404 is further configured to maintain the micro-overlay nodes 416, 418, 608, 610, and 612 in the executable graph-based model 100. In another embodiment, the executable active node is further configured to maintain a first subset of micro-overlay nodes of the first set of micro-overlay nodes, in the executable graph-based model 100, and one or more executable node elements, of the active node 302, are configured to maintain a second subset of micro-overlay nodes of the first set of micro-overlay nodes, in the executable graph-based model 100. In an example, the executable active node maintains the micro-overlay nodes 416, 418, and 608, an executable label maintains the micro-overlay node 610 and an executable icon maintains the micro-overlay node 612. In yet another embodiment, each executable node element is configured to maintain the corresponding micro-overlay node, in the executable graph-based model 100.

Although FIG. 6A illustrates in-situ data processing in a non-templated version of the executable graph-based model 100, the scope of the present disclosure is not limited to it. In other embodiments, in-situ data processing may be similarly facilitated in the templated version of the executable graph-based model 100, without deviating from the scope of the present disclosure.

Figure 6B:
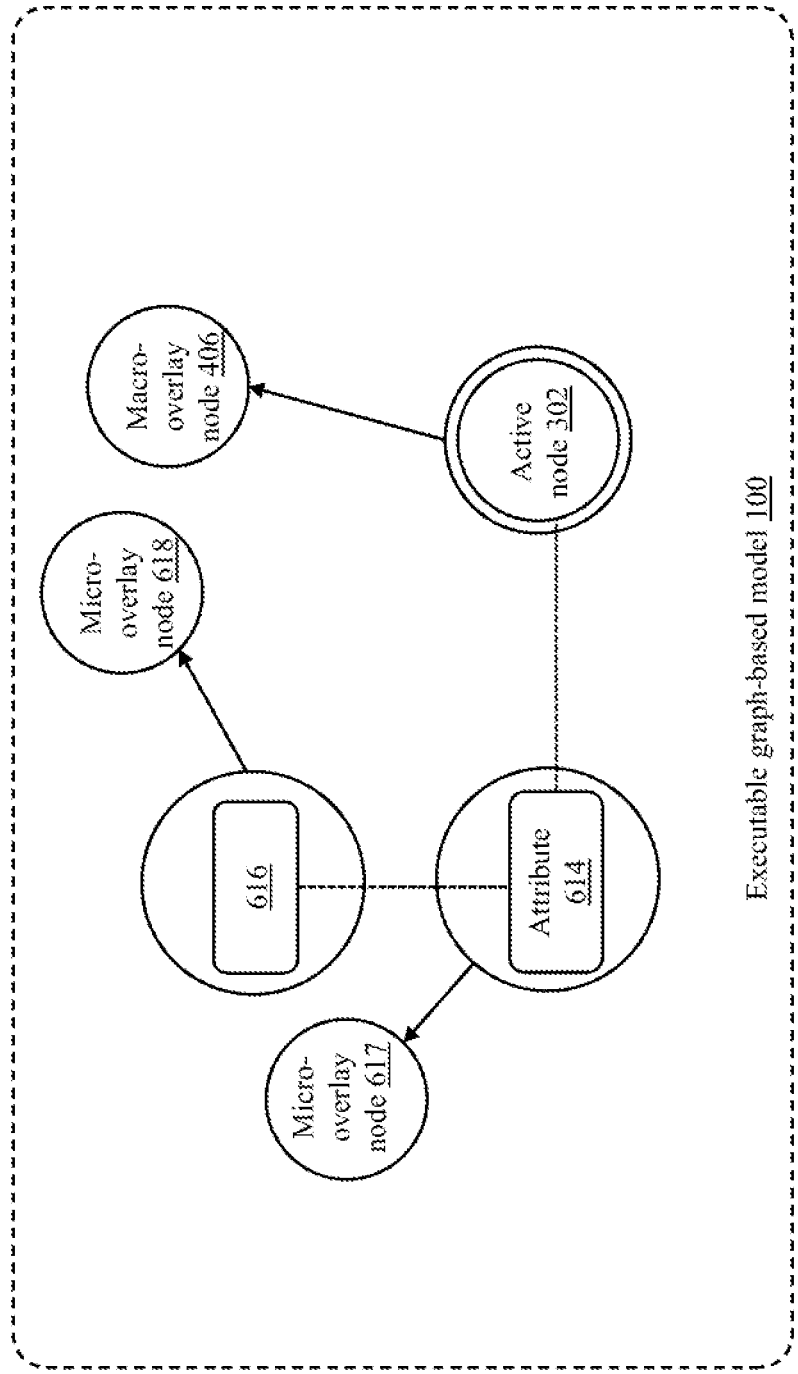
FIG. 6B is a schematic diagram that illustrates in-situ data processing in the overlay system using micro-overlays, in accordance with another embodiment of the present disclosure.

FIG. 6B is a schematic diagram 600B that illustrates in-situ data processing in the overlay system 202 using micro-overlays, in accordance with another embodiment of the present disclosure. The executable graph-based model 100 illustrates the active node 302 associated with the macro-overlay node 406. Further, at least one node element, of the first set of node elements of the active node 302, corresponds to an attribute 614 of the set of attributes 310. The attribute 614 corresponds to a value-shared attribute. That is to say, an attribute value object 616 is associated with the attribute 614 such that the attribute value object 616 may be shared with one or more active nodes in the executable graph-based model 100. Further, the attribute 614 is associated with a micro-overlay node 617 and the attribute value object 616 is associated with a micro-overlay node 618. That is to say, the micro-overlay node 617 extends functionality of the attribute 614 and the micro-overlay node 618 extends functionality of the attribute value object 616.

During the execution of the operation associated with the first stimulus, the stimuli management module 212, in conjunction with the context module 210, the controller module 206, and the overlay management module 214, may be further configured to identify at least the attribute 614 and the attribute value object 616 associated with the first set of node elements based on the first context of the first stimulus. The stimuli management module 212, in conjunction with the context module 210, the controller module 206, and the overlay management module 214, may be further configured to identify at least the micro-overlay node 617 associated with the attribute 614 and the micro-overlay node 618 associated with the attribute value object 616. The operation associated with the first stimulus may be executed further based on the attribute 614, the attribute value object 616, and the micro-overlay nodes 617 and 618. In such a scenario, the micro-overlay node 618 overrides the micro-overlay node 617 for the attribute value object 616 and the micro-overlay node 617 overrides the macro-overlay node 406 for the attribute 614. As a result, the micro-overlay node 617 is executed for the attribute 614 and the micro-overlay node 618 is executed for the attribute value object 616. Additionally, as the attribute value object 616 is shared between two or more active nodes, the micro-overlay node 618 may be executed during the execution of each of the two or more active nodes. Thus, the present disclosure enables the application of desired micro-overlay nodes to an attribute value object instead of applying the same to the corresponding entire node element and/or active node.

Although it is illustrated that one micro-overlay node is associated with the attribute value object 616, the scope of the present disclosure is not limited to it. In other embodiments, more than one micro-overlay node may be associated with the attribute value object 616.

Figure 6C:
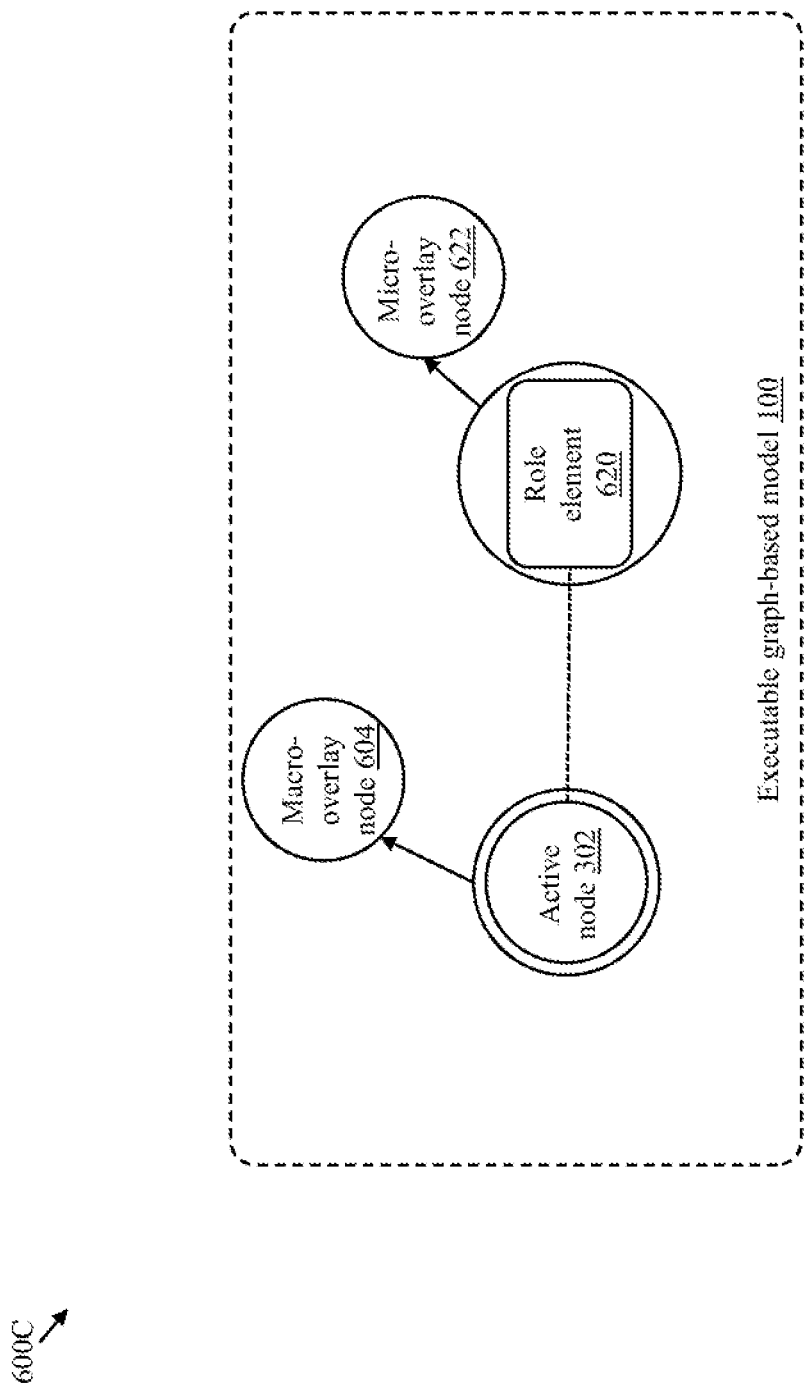
FIG. 6C is a schematic diagram that illustrates in-situ data processing in the overlay system using micro-overlays, in accordance with yet another embodiment of the present disclosure.

FIG. 6C is a schematic diagram 600C that illustrates in-situ data processing in the overlay system 202 using micro-overlays, in accordance with yet another embodiment of the present disclosure.

Referring to FIG. 6C, the active node 302 corresponds to an edge node. Further, at least one role element 620 is associated with the edge node. A role element is configured to define a relationship between two active nodes. Additionally, the role element 620 corresponds to a node element of the active node 302 (e.g., corresponds to a node element of the plurality of node elements associated with the active node 302). Thus, a micro-overlay node 622 is associated with the role element 620 to extend the functionality of the role element 620.

During the execution of the operation associated with the first stimulus, the stimuli management module 212, in conjunction with the context module 210, the controller module 206, and the overlay management module 214, may be further configured to identify the role element 620 and the micro-overlay node 622, based on the first context of the first stimulus. The operation associated with the first stimulus may be executed further based on the role element 620 and the micro-overlay node 622.

Although it is illustrated that one micro-overlay node is associated with the role element 620, the scope of the present disclosure is not limited to it. In other embodiments, more than one micro-overlay node may be associated with the role element 620.

In the present disclosure, data and processing logic are stored separately to ensure segregation and independent control thereof. Therefore, prior to the execution of the operation associated with the first stimulus, the data management module 234, in conjunction with the overlay management module 214, may be configured to determine that at least one of the active node 302, the macro-overlay node 406, and the micro-overlay nodes 416, 418, 608, 610, 612, 618, and 622 that are required for executing the operation associated with the first stimulus, is currently not loaded in the executable graph-based model 100. Thus, the data management module 234, in conjunction with the overlay management module 214, is configured to load at least one of the active node 302, the macro-overlay node 406, and the micro-overlay nodes 416, 418, 608, 610, 612, 618, and 622, in the executable graph-based model 100, with corresponding data and processing logic.

Figure 7:
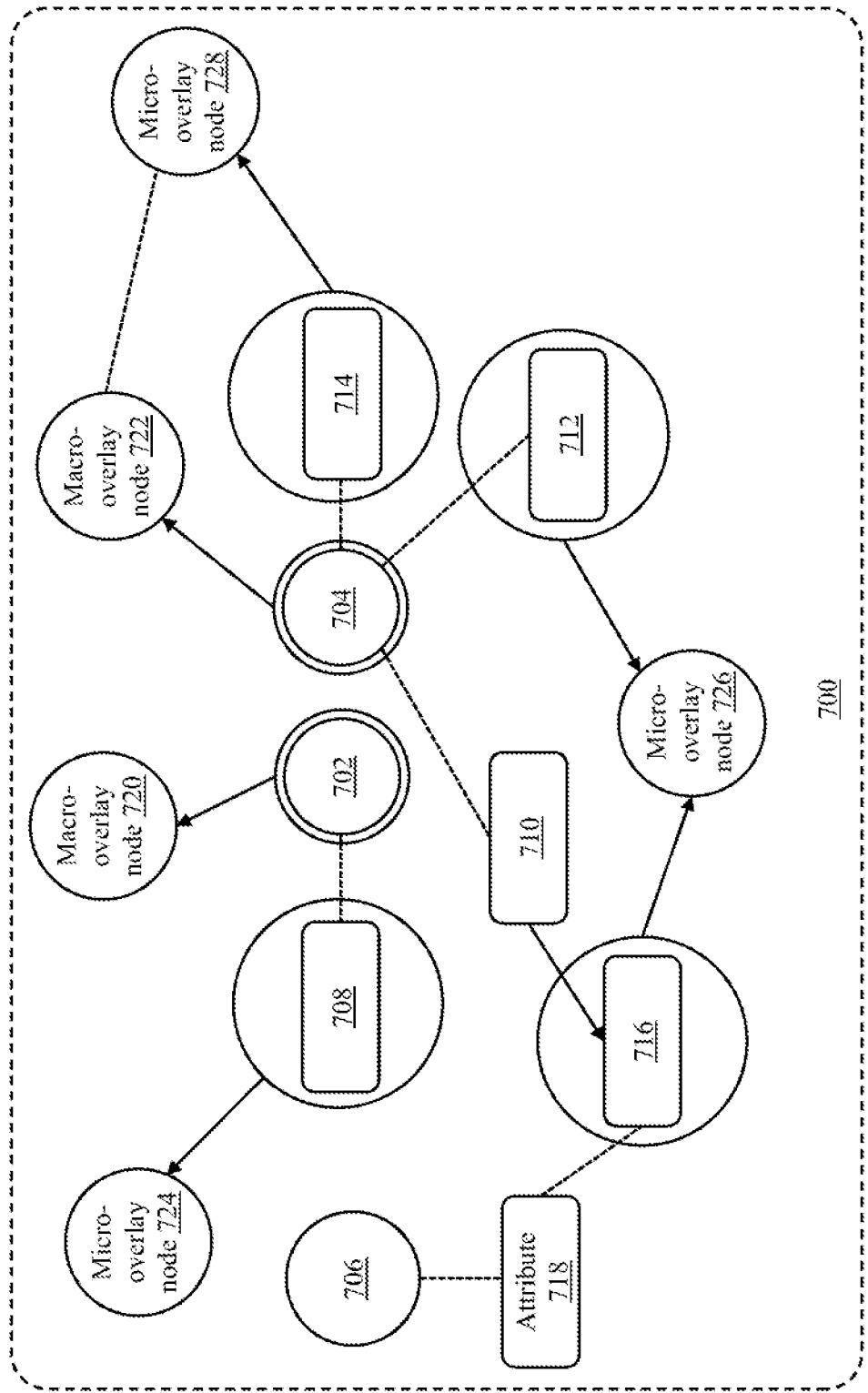
FIG. 7 is a schematic diagram that illustrates an implementation of in-situ data processing using micro-overlays, in accordance with an embodiment of the present disclosure.

FIG. 7 is a schematic diagram that illustrates an implementation of in-situ data processing using micro-overlays, in accordance with an embodiment of the present disclosure. Referring to FIG. 7, an executable graph-based medical system model 700 is illustrated. The executable graph-based medical system model 700 is hereinafter referred to as "the medical system model 700". The medical system model 700 includes patient data associated with various patients. The patient data may include personal details (such as name, age, gender, address, or the like), diagnostic details, details of the doctor, or the like, of each patient. The patient data may be utilized for various purposes such as to identify diseases, prescribe medicines, maintain patient history, or the like. Thus, various operations may be performed based on the patient's data. For the sake of ongoing discussion, it is assumed that the medical system model 700 includes a patient node 702, a patient node 704, and a patient node 706. Each of the patient nodes 702, 704, and 706 includes patient data associated with three different patients. Further, each of the patient nodes 702, 704, and 706 are structurally and functionally similar to the node 302 described in FIG. 3A.

The patient node 702 is shown to include an attribute 708. The attribute 708 corresponds to the social security number of a patient associated with the patient node 702. The attribute 708 is hereinafter referred to as "the social security number attribute 708". The patient node 704 is shown to include attributes 710, 712, and 714. The attribute 710 corresponds to a value shared attribute and is associated with a value object 716. The value object 716 corresponds to the name of a doctor associated with the patient node 704. Additionally, the patient node 706 includes an attribute 718 which is also associated with the value object 716. The attributes 710 and 718 are value-shared attributes as the attributes 710 and 718 share the value object 716. The value object 716 is hereinafter referred to as the "doctor object 716". The attribute 712 corresponds to a glucose level and thus is hereinafter referred to as the "glucose level attribute 712". Further, the attribute 714 corresponds to an address associated with the patient node 704. The attribute 714 is hereinafter referred to as the "address attribute 714".

The patient node 702 is associated with a macro-overlay node 720. That is to say, the macro-overlay node 720 is an overlay of the patient node 702. The macro-overlay node 720 corresponds to an encryption overlay node. Thus, the macro-overlay node 720 is configured to encrypt the patient node 702. The patient node 704 is associated with a macro-overlay node 722. The macro-overlay node 720 corresponds to an encryption overlay node. Thus, the macro-overlay node 722 is configured to encrypt the patient node 704. Further, the social security number attribute 708 is associated with a micro-overlay node 724. That is to say, the micro-overlay node 724 is an overlay of the social security number attribute 708. The micro-overlay node 724 corresponds to an encryption overlay node. Thus, the micro-overlay node 724 is configured to encrypt the social security number attribute 708. An encryption strategy of the micro-overlay node 724 is different from an encryption strategy of the macro-overlay node 720. Also, the encryption strategy of the micro-overlay node 724 is stronger than the encryption strategy of the macro-overlay node 720. Thus, in a scenario where encryption based on the macro-overlay node 720 is bypassed, the social security number attribute 708 is still encrypted.

The glucose level attribute 712 and the doctor object 716 are associated with a micro-overlay 726. That is to say, the micro-overlay node 726 is an overlay of glucose level attribute 712 and the doctor object 716. The micro-overlay node 726 corresponds to an encryption overlay node. Thus, the micro-overlay node 726 is configured to encrypt the glucose level attribute 712 and the doctor object 716. Additionally, an encryption strategy of the micro-overlay node 726 is different from an encryption strategy of the macro-overlay node 722. Further, the address attribute 714 is associated with a micro-overlay node 728. That is to say, the micro-overlay node 728 is an overlay of the address attribute 714. The micro-overlay node 728 corresponds to an encryption overlay node. Thus, the micro-overlay node 728 is configured to encrypt the address attribute 714. An encryption strategy of the micro-overlay node 728 is different from an encryption strategy of the macro-overlay node 722. FIG. 7 illustrates an association between the macro-overlay node 722 and the micro-overlay node 728. The association indicates that the macro-overlay node 722 stores association data that is indicative of the association of the micro-overlay node 728 with the address attribute 714. However, the association data is not indicative of the association of the micro-overlay node 726 with the glucose level attribute 712 and the doctor object 716.

In operation, the stimuli management module 212 may receive a second stimulus of the set of stimuli 228. The second stimulus corresponds to a command. The second stimulus indicates encryption of the patient nodes 702, 704, and 706. The stimuli management module 212, in conjunction with the controller module 206 and the context module 210, may identify the patient nodes 702, 704, and 706, in the medical system model 700. Further, the controller module 206, in conjunction with the overlay management module 214, may identify the macro-overlay node 720 and the macro-overlay node 722 associated with the patient nodes 702 and 704, respectively, based on a second context of the second stimulus. The controller module 206, in conjunction with the overlay management module 214, may execute an operation associated with the second stimulus.

During the execution of the operation associated with the second stimulus, the macro-overlay node 720 may determine that the social security number attribute 708 is associated with the micro-overlay node 724. Thus, the micro-overlay node 724 is executed for the social security number attribute 708. In an example, the macro-overlay node 720 may determine the association of the micro-overlay node 724 with the social security number attribute 708, by communicating with an overlay manager of the active node 702. That is to say, the micro-overlay node 724 overrides the macro-overlay node 720 for the social security number attribute 708. Moreover, the macro-overlay node 720 is executed for other node elements of the patient node 702 based on an absence of association of a micro-overlay node with the corresponding node element. Further, the macro-overlay node 722 determines that the glucose level attribute 712 and the doctor object 716 are associated with the micro-overlay node 726. Thus, the micro-overlay node 726 is executed for the glucose level attribute 712 and the doctor object 716. That is to say, the micro-overlay node 726 overrides the macro-overlay node 722 for the glucose level attribute 712 and the doctor object 716.

As mentioned previously, based on the association data that is indicative of the association of the micro-overlay node 728 with the address attribute 714 (shown by way of a dotted line between the macro-overlay node 722 and the micro-overlay node 724), the macro-overlay node 722 is aware of the association of the micro-overlay node 728 with the address attribute 714. Thus, the micro-overlay node 728 is executed for the address attribute 714. That is to say, the micro-overlay node 728 overrides the macro-overlay node 722 for the address attribute 714. Further, the macro-overlay node 722 is executed for other node elements of the patient node 704. In such a scenario, as no micro-overlay node is associated with the attribute 710, the macro-overlay node 722 is executed for the attribute 710. That is to say, the attribute 710 is encrypted based on the macro-overlay node 722. Thus, the execution of the operation associated with the second stimulus results in the encryption of the patient nodes 702, 704, and 706.

Throughout the description, each node that is represented in a corresponding figure as an inner circle enclosed within an outer circle is an executable node. The inner circle represents its base node, and the outer circle represents an overlay node associated therewith. Further, each node element that is represented in a corresponding figure as an inner rectangle enclosed within an outer circle is an executable node element. A coupling between the outer circle and a node indicates that the node is an overlay of the executable node and/or the executable node element.

Figure 8:
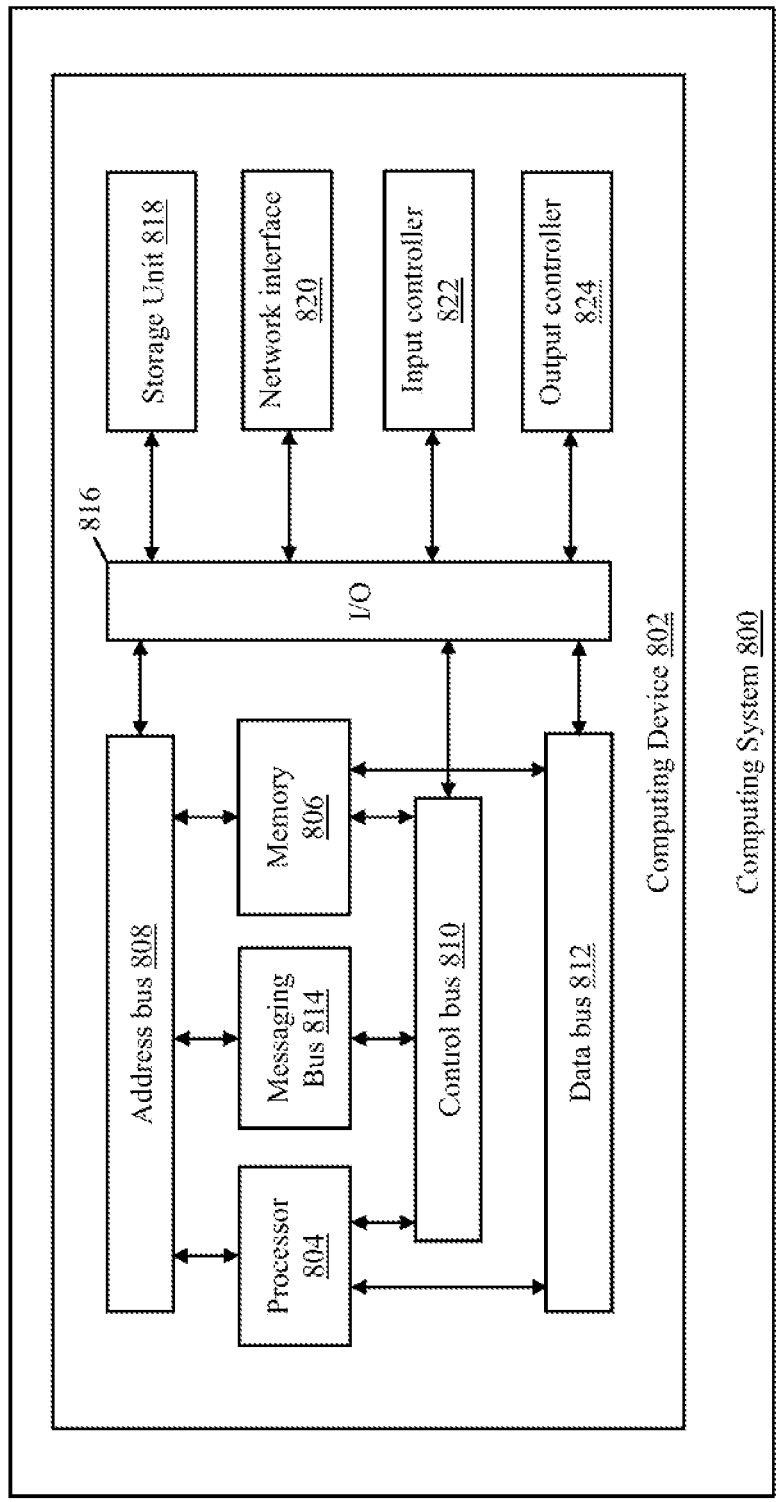
FIG. 8 shows an example computing system for carrying out the methods of the present disclosure, in accordance with an embodiment of the present disclosure.

FIG. 8 shows an example computing system 800 for carrying out the methods of the present disclosure, in accordance with an embodiment of the present disclosure. Specifically, FIG. 8 shows a block diagram of an embodiment of the computing system 800 according to example embodiments of the present disclosure.

The computing system 800 may be configured to perform any of the operations disclosed herein, such as, for example, any of the operations discussed with reference to the functional modules described in relation to FIG. 2. The computing system 800 can be implemented as a conventional computer system, an embedded controller, a laptop, a server, a mobile device, a smartphone, a set-top box, a kiosk, a vehicular information system, one or more processors associated with a television, a customized machine, any other hardware platform, or any combination or multiplicity thereof. In one embodiment, the computing system 800 is a distributed system configured to function using multiple computing machines interconnected via a data network or bus system.

The computing system 800 includes computing devices (such as a computing device 802). The computing device 802 includes one or more processors (such as a processor 804) and a memory 806. The processor 804 may be any general-purpose processor(s) configured to execute a set of instructions. For example, the processor 804 may be a processor core, a multiprocessor, a reconfigurable processor, a microcontroller, a digital signal processor (DSP), an application-specific integrated circuit (ASIC), a graphics processing unit (GPU), a neural processing unit (NPU), an accelerated processing unit (APU), a brain processing unit (BPU), a data processing unit (DPU), a holographic processing unit (HPU), an intelligent processing unit (IPU), a microprocessor/microcontroller unit (MPU/MCU), a radio processing unit (RPU), a tensor processing unit (TPU), a vector processing unit (VPU), a wearable processing unit (WPU), a field programmable gate array (FPGA), a programmable logic device (PLD), a controller, a state machine, gated logic, discrete hardware component, any other processing unit, or any combination or multiplicity thereof. In one embodiment, the processor 804 may be multiple processing units, a single processing core, multiple processing cores, special purpose processing cores, co-processors, or any combination thereof. The processor 804 may be communicatively coupled to the memory 806 via an address bus 808, a control bus 810, a data bus 812, and a messaging bus 814.

The memory 806 may include non-volatile memories such as a read-only memory (ROM), a programmable read-only memory (PROM), an erasable programmable read-only memory (EPROM), a flash memory, or any other device capable of storing program instructions or data with or without applied power. The memory 806 may also include volatile memories, such as a random-access memory (RAM), a static random-access memory (SRAM), a dynamic random-access memory (DRAM), and a synchronous dynamic random-access memory (SDRAM). The memory 806 may include single or multiple memory modules. While the memory 806 is depicted as part of the computing device 802, a person skilled in the art will recognize that the memory 806 can be separate from the computing device 802.

The memory 806 may store information that can be accessed by the processor 804. For instance, the memory 806 (e.g., one or more non-transitory computer-readable storage mediums, memory devices) may include computer-readable instructions (not shown) that can be executed by the processor 804. The computer-readable instructions may be software written in any suitable programming language or may be implemented in hardware. Additionally, or alternatively, the computer-readable instructions may be executed in logically and/or virtually separate threads on the processor 804. For example, the memory 806 may store instructions (not shown) that when executed by the processor 804 cause the processor 804 to perform operations such as any of the operations and functions for which the computing system 800 is configured, as described herein. Additionally, or alternatively, the memory 806 may store data (not shown) that can be obtained, received, accessed, written, manipulated, created, and/or stored. The data can include, for instance, the data and/or information described herein in relation to FIGS. 1-7. In some implementations, the computing device 802 may obtain from and/or store data in one or more memory device(s) that are remote from the computing system 800.

The computing device 802 may further include an input/output (I/O) interface 816 communicatively coupled to the address bus 808, the control bus 810, and the data bus 812. The data bus 812 and messaging bus 814 may include a plurality of tunnels that may support parallel execution of messages by the overlay system 202. The I/O interface 816 is configured to couple to one or more external devices (e.g., to receive and send data from/to one or more external devices). Such external devices, along with the various internal devices, may also be known as peripheral devices. The I/O interface 816 may include both electrical and physical connections for operably coupling the various peripheral devices to the computing device 802. The I/O interface 816 may be configured to communicate data, addresses, and control signals between the peripheral devices and the computing device 802. The I/O interface 816 may be configured to implement any standard interface, such as a small computer system interface (SCSI), a serial-attached SCSI (SAS), a fiber channel, a peripheral component interconnect (PCI), a PCI express (PCIe), a serial bus, a parallel bus, an advanced technology attachment (ATA), a serial ATA (SATA), a universal serial bus (USB), Thunderbolt, FireWire, various video buses, and the like. The I/O interface 816 is configured to implement only one interface or bus technology. Alternatively, the I/O interface 816 is configured to implement multiple interfaces or bus technologies. The I/O interface 816 may include one or more buffers for buffering transmissions between one or more external devices, internal devices, the computing device 802, or the processor 804. The I/O interface 816 may couple the computing device 802 to various input devices, including mice, touch screens, scanners, biometric readers, electronic digitizers, sensors, receivers, touchpads, trackballs, cameras, microphones, keyboards, any other pointing devices, or any combinations thereof. The I/O interface 816 may couple the computing device 802 to various output devices, including video displays, speakers, printers, projectors, tactile feedback devices, automation control, robotic components, actuators, motors, fans, solenoids, valves, pumps, transmitters, signal emitters, lights, and so forth.

The computing system 800 may further include a storage unit 818, a network interface 820, an input controller 822, and an output controller 824. The storage unit 818, the network interface 820, the input controller 822, and the output controller 824 are communicatively coupled to the central control unit (e.g., the memory 806, the address bus 808, the control bus 810, and the data bus 812) via the I/O interface 816. The network interface 820 communicatively couples the computing system 800 to one or more networks such as wide area networks (WAN), local area networks (LAN), intranets, the Internet, wireless access networks, wired networks, mobile networks, telephone networks, optical networks, or combinations thereof. The network interface 820 may facilitate communication with packet-switched networks or circuit-switched networks which use any topology and may use any communication protocol. Communication links within the network may involve various digital or analog communication media such as fiber optic cables, free-space optics, waveguides, electrical conductors, wireless links, antennas, radio-frequency communications, and so forth.

The storage unit 818 is a computer-readable medium, preferably a non-transitory computer-readable medium, comprising one or more programs, the one or more programs comprising instructions which when executed by the processor 804 cause the computing system 800 to perform the method steps of the present disclosure. Alternatively, the storage unit 818 is a transitory computer-readable medium. The storage unit 818 can include a hard disk, a floppy disk, a compact disc read-only memory (CD-ROM), a digital versatile disc (DVD), a Blu-ray disc, a magnetic tape, a flash memory, another non-volatile memory device, a solid-state drive (SSD), any magnetic storage device, any optical storage device, any electrical storage device, any semiconductor storage device, any physical-based storage device, any other data storage device, or any combination or multiplicity thereof. In one embodiment, the storage unit 818 stores one or more operating systems, application programs, program modules, data, or any other information. The storage unit 818 is part of the computing device 802. Alternatively, the storage unit 818 is part of one or more other computing machines that are in communication with the computing device 802, such as servers, database servers, cloud storage, network attached storage, and so forth.

The input controller 822 may include suitable logic, circuitry, interfaces, and/or code, executable by the circuitry, that may be configured to control one or more input devices that may be configured to receive an input (the set of stimuli 228) for the overlay system 202. The output controller 824 may include suitable logic, circuitry, interfaces, and/or code, executable by the circuitry, that may be configured to control one or more output devices that may be configured to render/output the outcome of the operation executed to process the received input (the set of stimuli 228).

Figure 9A:
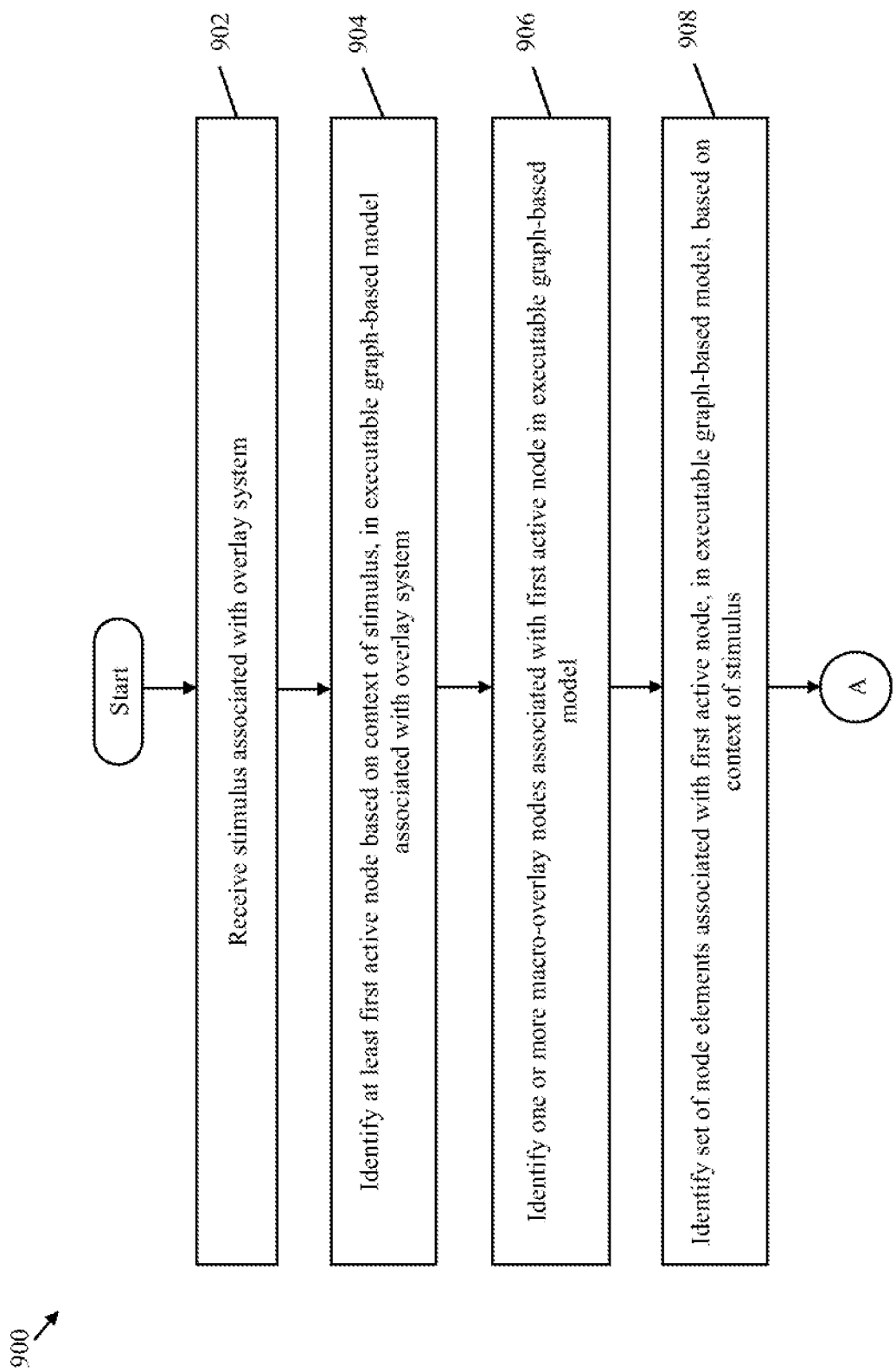
FIGS. 9A and 9B, collectively, represents a flowchart that illustrates a method for facilitating in-situ data processing in the overlay system using micro-overlays, in accordance with an embodiment of the present disclosure.
Figure 9B:
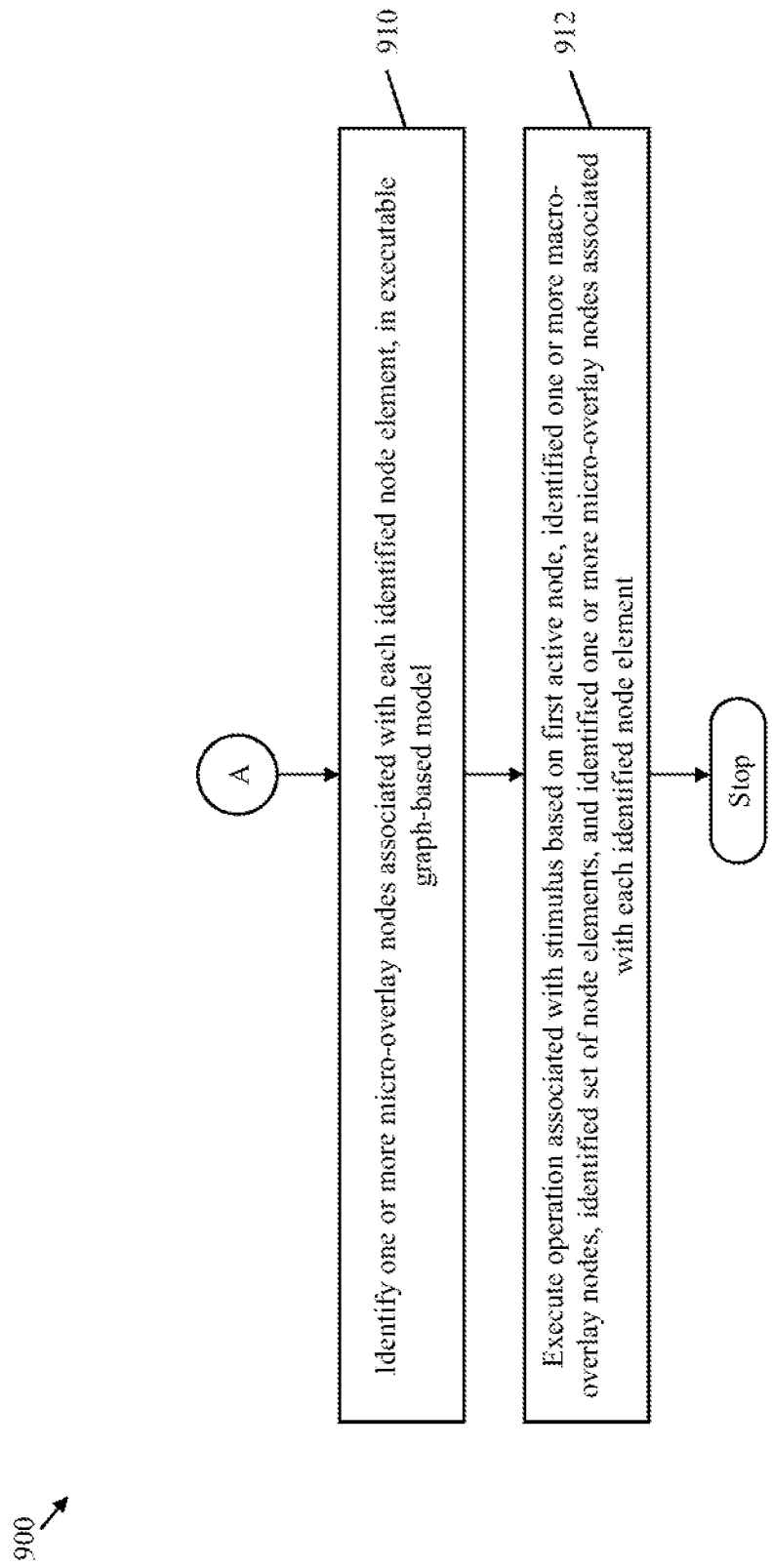

FIGS. 9A and 9B, collectively, represents a flowchart 900 that illustrates a method for facilitating in-situ data processing in the overlay system 202 using micro-overlays, in accordance with an embodiment of the present disclosure.

Referring to FIG. 9A, at 902, the processing circuitry (e.g., the stimuli management module 212) receives a stimulus (e.g., the first stimulus) associated with the overlay system 202. The stimulus may correspond to a command or a query. At 904, the processing circuitry (e.g., the controller module 206, in conjunction with stimuli management module 212), identifies at least a first active node (e.g., the active node 302) in the executable graph-based model 100 based on a context of the received stimulus.

At 906, the processing circuitry (e.g., the controller module 206, in conjunction with the overlay management module 214) identifies one or more macro-overlay nodes (e.g., the macro-overlay node 406) associated with the first active node in the executable graph-based model 100 based on the first context of the first stimulus. At 908, the processing circuitry (e.g., the controller module 206, in conjunction with the overlay management module 214) identifies a set of node elements (e.g., the metadata 312, the attribute 412, the label 604, and the icon 606) associated with the first active node, in the executable graph-based model 100, based on the context of the stimulus.

Referring to FIG. 9B, at 910, the processing circuitry (e.g., the controller module 206, in conjunction with the overlay management module 214) identifies one or more micro-overlay nodes (e.g., the micro-overlay node 608) associated with each identified node element, in the executable graph-based model 100. At 912, the processing circuitry (e.g., the controller module 206, in conjunction with the overlay management module 214) is further configured to execute an operation associated with the stimulus based on the first active node, the identified one or more macro-overlay nodes, the identified set of node elements, and the identified one or more micro-overlay nodes associated with each identified node element.

The disclosed embodiments encompass numerous advantages including an efficient and seamless approach for facilitation of in-situ data processing in overlay systems using micro-overlays. As data and processing logic are in-situ in the overlay system at run-time, time complexity and processing complexity associated with data processing are significantly reduced. The reduction in time complexity is beneficial in applications such as healthcare, finance, and robotics that involve time-critical operations. Additionally, the functionality of node elements associated with nodes is extended by the use of micro-overlays in the overlay system. Thus, the overlay system is highly flexible as processing logic can be applied to desirable node elements and operations based on processing logic can be executed only on the desirable node elements. Further, the disclosed systems and methods do not require the data and processing logic to be available at all times, and hence, the data and processing logic when not in use may be stored separately and re-loaded in the corresponding executable node when needed. Thus, the systems and methods disclosed herein provide an efficient approach for in-situ data processing in overlay systems using micro-overlays.

A person of ordinary skill in the art will appreciate that embodiments and exemplary scenarios of the disclosed subject matter may be practiced with various computer system configurations, including multi-core multiprocessor systems, minicomputers, mainframe computers, computers linked or clustered with distributed functions, as well as pervasive or miniature computers that may be embedded into virtually any device. Further, the operations may be described as a sequential process, however, some of the operations may be performed in parallel, concurrently, and/or in a distributed environment, and with program code stored locally or remotely for access by single or multiprocessor machines. In addition, in some embodiments, the order of operations may be rearranged without departing from the spirit of the disclosed subject matter.

Certain embodiments of the disclosure may be found in the disclosed systems, methods, and non-transitory computer-readable medium, for facilitating in-situ data processing in overlay systems using micro-overlays. The methods and systems disclosed herein include various operations performed by the processing circuitry (e.g., the controller module 206, the context module 210, the stimuli management module 212, the overlay management module 214, any other element of the overlay system 202, or a combination of two or more elements of the overlay system 202). The overlay system disclosed herein includes the storage element configured to store an executable graph-based model that comprises a plurality of active nodes, where each active node comprises a plurality of node elements. The executable graph-based model further includes a set of micro-overlay nodes associated with each active node of the plurality of active nodes, such that each micro-overlay node is associated with at least one node element, of the plurality of node elements, and is configured to extend the functionality of the corresponding node element. Further, the processing circuitry is coupled to the storage element, and configured to receive a first stimulus associated with the overlay system. The processing circuitry is further configured to identify, in the executable graph-based model, based on a first context of the first stimulus, at least a first active node. The processing circuitry is further configured to identify, based on the first context of the first stimulus, (i) a first set of node elements from a first plurality of node elements of the first active node, and one or more micro-overlay nodes associated with each identified node element, that are required for processing of the first stimulus. Additionally, the processing circuitry executes an operation associated with the first stimulus based on the identified first set of node elements and the identified one or more micro-overlay nodes associated with each identified node element.

In some embodiments, the executable graph-based model further comprises a plurality of macro-overlay nodes, where each active node, of the plurality of active nodes, is associated with a set of macro-overlay nodes of the plurality of macro-overlay nodes, such that each macro-overlay node, of the set of macro-overlay nodes, is configured to extend functionality of the corresponding active node. Further, the processing circuitry is configured to identify, for the processing of the first stimulus, one or more macro-overlay nodes from a first set of macro-overlay nodes associated with the first active node, that are required for processing of the first stimulus. Additionally, the processing circuitry executes the operation associated with the first stimulus further based on the first active node and the identified one or more macro-overlay nodes.

In some embodiments, the first plurality of node elements of the first active node further comprises a second set of node elements. During the execution of the operation associated with the first stimulus, for each node element of the first set of node elements, the corresponding one or more micro-overlay nodes are executed, whereas, for each node element of the second set of node elements, the one or more macro-overlay nodes associated with the first active node are executed.

In some embodiments, during the execution of the operation associated with the first stimulus, the processing circuitry is further configured to determine, for each node element of the first plurality of node elements, whether the corresponding node element is associated with at least one micro-overlay node. Further, the one or more macro-overlay nodes associated with the first active node are executed for each node element of the second set of node elements based on an absence of association of a micro-overlay node with the corresponding node element.

In some embodiments, the one or more macro-overlay nodes associated with the first active node are configured to store association data that is indicative of the association of at least one micro-overlay node with each of the first set of node elements. Further, the one or more macro-overlay nodes are executed for each node element of the second set of node elements based on an absence of association of a micro-overlay node with the corresponding node element.

In some embodiments, the one or more macro-overlay nodes, associated with the first active node, are executed prior to the execution of the one or more micro-overlay nodes associated with each identified node element of the first plurality of node elements.

In some embodiments, the one or more macro-overlay nodes, associated with the first active node, are executed after the execution of the one or more micro-overlay nodes associated with each identified node element of the first set of node elements.

In some embodiments, the first active node and the first set of macro-overlay nodes associated therewith constitute a first executable active node. Further, the first executable active node is configured to maintain the first set of macro-overlay nodes, in the executable graph-based model.

In some embodiments, the first executable active node is further configured to maintain the first plurality of micro-overlay nodes associated with the first active node, in the executable graph-based model.

In some embodiments, each node element, of the first set of node elements, and at least one micro-overlay node associated therewith constitute an executable node element. Additionally, the first executable active node is further configured to maintain a first subset of micro-overlay nodes of the first set of micro-overlay nodes, in the executable graph-based model. Further, one or more executable node elements, of the first active node, are configured to maintain a second subset of micro-overlay nodes of the first set of micro-overlay nodes, in the executable graph-based model.

In some embodiments, each node element, of the first set of node elements, and at least one micro-overlay node associated therewith constitute an executable node element that is configured to maintain the corresponding micro-overlay node, in the executable graph-based model.

In some embodiments, the plurality of node elements comprise at least two of a group consisting of a unique identifier, a version identifier, a namespace, a name, a set of icons, a set of labels, an alternate identifier, a set of attributes, metadata, a node configuration, a node configuration extension, and node configuration strategies.

In some embodiments, at least one node element, of the first set of node elements, corresponds to an attribute, and an attribute value object is associated with the attribute. Additionally, at least one micro-overlay node is associated with the attribute value object.

In some embodiments, during the execution of the operation associated with the first stimulus, the processing circuitry is further configured to identify at least a first attribute value object associated with the first set of node elements based on the first context of the first stimulus. Additionally, at least a first micro-overlay node is associated with the first attribute value object, and the processing circuitry executes the operation associated with the first stimulus further based on the first attribute value object and the first micro-overlay node.

In some embodiments, each active node of the plurality of active nodes corresponds to one of a group consisting of a vertex node, an edge node, a role node, a micro-overlay node, and a macro-overlay node.

In some embodiments, at least one active node, of the plurality of active nodes, corresponds to an edge node with at least one role element being associated with the edge node, and the role element corresponds to a node element of the corresponding active node.

In some embodiments, each of the plurality of active nodes and the associated set of micro-overlay nodes comprises a node template that corresponds to a predefined node structure and a node instance that corresponds to an implementation of the node template.

In some embodiments, the first stimulus corresponds to one of a group consisting of a command and a query.

In some embodiments, prior to the execution of the operation associated with the first stimulus, the processing circuitry is further configured to load, in the executable graph-based model, one of a group consisting of a first active node that comprises the first set of node elements and one or more micro-overlay nodes associated with each identified node element, with corresponding data and processing logic.

Moreover, for example, the present technology/system may achieve the following configurations:

1. An overlay system, comprising:
   a storage element configured to store an executable graph-based model that comprises:

a plurality of active nodes, where each active node comprises a plurality of node elements; and a set of micro-overlay nodes associated with each active node of the plurality of active nodes, such that each micro-overlay node is associated with at least one node element, of the plurality of node elements, and is configured to extend functionality of the corresponding node element; and processing circuitry that is coupled to the storage element, and configured to:

receive a first stimulus associated with the overlay system;

identify, in the executable graph-based model, based on a first context of the first stimulus, at least a first active node;

identify, based on the first context of the first stimulus, (i) a first set of node elements, from a first plurality of node elements of the first active node, and (ii) one or more micro-overlay nodes associated with each identified node element, that are required for processing of the first stimulus; and execute an operation associated with the first stimulus based on the identified first set of node elements and the identified one or more micro-overlay nodes associated with each identified node element.

2. The overlay system of 1, wherein the executable graph-based model further comprises a plurality of macro-overlay nodes, where each active node, of the plurality of active nodes, is associated with a set of macro-overlay nodes of the plurality of macro-overlay nodes, such that each macro-overlay node, of the set of macro-overlay nodes, is configured to extend functionality of the corresponding active node, wherein the processing circuitry is further configured to identify, for the processing of the first stimulus, one or more macro-overlay nodes from a first set of macro-overlay nodes associated with the first active node, that are required for processing of the first stimulus, and wherein the processing circuitry executes the operation associated with the first stimulus further based on the first active node and the identified one or more macro-overlay nodes.

3. The overlay system of 2, wherein the first plurality of node elements of the first active node further comprises a second set of node elements, and wherein during the execution of the operation associated with the first stimulus, for each node element of the first set of node elements, the corresponding one or more micro-overlay nodes are executed, whereas, for each node element of the second set of node elements, the one or more macro-overlay nodes associated with the first active node are executed.

4. The overlay system of 3, wherein during the execution of the operation associated with the first stimulus, the processing circuitry is further configured to determine, for each node element of the first plurality of node elements, whether the corresponding node element is associated with at least one micro-overlay node, and wherein the one or more macro-overlay nodes associated with the first active node are executed for each node element of the second set of node elements based on an absence of association of a micro-overlay node with the corresponding node element.

5. The overlay system of 3, wherein the one or more macro-overlay nodes associated with the first active node are configured to store association data that is indicative of the association of at least one micro-overlay node with each of the first set of node elements, and wherein the one or more macro-overlay nodes are executed for each node element of the second set of node elements based on an absence of association of a micro-overlay node with the corresponding node element.

6. The overlay system of 2, wherein the one or more macro-overlay nodes, associated with the first active node, are executed prior to the execution of the one or more micro-overlay nodes associated with each identified node element of the first active node.

7. The overlay system of 2, wherein the one or more macro-overlay nodes, associated with the first active node, are executed after the execution of the one or more micro-overlay nodes associated with each identified node element of the first set of node elements.

8. The overlay system of 2, wherein the first active node and the first set of macro-overlay nodes associated therewith constitute a first executable active node, and wherein the first executable active node is configured to maintain the first set of macro-overlay nodes, in the executable graph-based model.

9. The overlay system of 8, wherein the first executable active node is further configured to maintain the first plurality of micro-overlay nodes associated with the first active node, in the executable graph-based model.

10. The overlay system of 8, wherein each node element, of the first set of node elements, and at least one micro-overlay node associated therewith constitute an executable node element, wherein the first executable active node is further configured to maintain a first subset of micro-overlay nodes of the first set of micro-overlay nodes, in the executable graph-based model, and wherein one or more executable node elements, of the first active node, are configured to maintain a second subset of micro-overlay nodes of the first set of micro-overlay nodes, in the executable graph-based model.

11. The overlay system of 2, wherein each of the identified one or more micro-overlay nodes and the identified one or more macro-overlay nodes is associated with different processing logic.

12. The overlay system of 2, wherein at least one micro-overlay node, of the plurality of micro-overlay nodes, is derived from one or more remaining micro-overlay nodes of the plurality of micro-overlay nodes, and wherein at least one macro-overlay node, of the plurality of macro-overlay nodes, is derived from one or more remaining macro-overlay nodes of the plurality of macro-overlay nodes.

13. The overlay system of 1, wherein each node element, of the first set of node elements, and at least one micro-overlay node associated therewith constitute an executable node element that is configured to maintain the corresponding micro-overlay node, in the executable graph-based model.

14. The overlay system of 1, wherein the plurality of node elements comprise at least two of a group consisting of a unique identifier, a version identifier, a namespace, a name, a set of icons, a set of labels, an alternate identifier, a set of attributes, metadata, a node configuration, a node configuration extension, and node configuration strategies.

15. The overlay system of 1,
wherein at least one node element, of the first set of node elements, corresponds to an attribute,
wherein an attribute value object is associated with the attribute, and
wherein at least one micro-overlay node is associated with the attribute value object.

16. The overlay system of 15, wherein during the execution of the operation associated with the first stimulus, the processing circuitry is further configured to identify (i) at least a first attribute value object associated with the first set of node elements based on the first context of the first stimulus and (ii) at least a first micro-overlay node associated with the first attribute value object, and wherein the processing circuitry executes the operation associated with the first stimulus further based on the first attribute value object and the first micro-overlay node.

17. The overlay system of 1, wherein each active node of the plurality of active nodes corresponds to one of a group consisting of a vertex node, an edge node, a role node, a micro-overlay node, and a macro-overlay node.

18. The overlay system of 1, wherein at least one active node, of the plurality of active nodes, corresponds to an edge node with at least one role element being associated with the edge node, and wherein the role element corresponds to a node element of the corresponding active node.

19. The overlay system of 1, wherein each of the plurality of active nodes and the associated set of micro-overlay nodes comprises a node template that corresponds to a predefined node structure and a node instance that corresponds to an implementation of the node template.

20. The overlay system of 1, wherein the first stimulus corresponds to one of a group consisting of a command and a query.

21. The overlay system of 1, wherein prior to the execution of the operation associated with the first stimulus, the processing circuitry is further configured to load, in the executable graph-based model, one of a group consisting of a first active node that comprises the first set of node elements and one or more micro-overlay nodes associated with each identified node element, with corresponding data and processing logic.

22. A method, comprising:
receiving, by processing circuitry of an overlay system, a first stimulus associated with the overlay system, wherein an executable graph-based model is stored in a storage element of the overlay system, and wherein the executable graph-based model comprises:
a plurality of active nodes, where each active node comprises a plurality of node elements; and
a set of micro-overlay nodes associated with each active node of the plurality of active nodes, such that each micro-overlay node is associated with at least one node element, of the plurality of node elements, to extend functionality of the corresponding node element;
identifying, by the processing circuitry, in the executable graph-based model, based on a first context of the first stimulus, at least a first active node, a first set of node elements, and one or more micro-overlay nodes associated with each identified node element, wherein the first active node comprises the first set of node elements; and
executing, by the processing circuitry, an operation associated with the first stimulus based on the identified first set of node elements and the identified one or more micro-overlay nodes associated with each identified node element.

What is claimed is:
1. An overlay system, comprising:
a storage element configured to store an executable graph-based model that comprises:
a plurality of active nodes, where each active node comprises a plurality of node elements; and
a plurality of micro-overlay nodes associated with each active node of the plurality of active nodes, such that each micro-overlay node is associated with at least one node element, of the plurality of node elements, and is configured to extend functionality of the corresponding node element; and
processing circuitry that is coupled to the storage element, and configured to:
receive a first stimulus associated with the overlay system;
identify, in the executable graph-based model, based on a first context of the first stimulus, at least a first active node;
identify, based on the first context of the first stimulus, (i) a first set of node elements from a first plurality of node elements of the first active node, and (ii) one or more micro-overlay nodes associated with each identified node element, that are required for processing of the first stimulus; and
execute an operation associated with the first stimulus based on the identified first set of node elements and the identified one or more micro-overlay nodes associated with each identified node element.

2. The overlay system of claim 1,
wherein the executable graph-based model further comprises a plurality of macro-overlay nodes, where each active node, of the plurality of active nodes, is associated with a set of macro-overlay nodes of the plurality of macro-overlay nodes, such that each macro-overlay node, of the set of macro-overlay nodes, is configured to extend functionality of the corresponding active node,
wherein the processing circuitry is further configured to identify, for the processing of the first stimulus, one or more macro-overlay nodes from a first set of macro-overlay nodes associated with the first active node, that are required for processing of the first stimulus, and
wherein the processing circuitry executes the operation associated with the first stimulus further based on the first active node and the identified one or more macro-overlay nodes.

3. The overlay system of claim 2,
wherein the first plurality of node elements of the first active node further comprises a second set of node elements, and
wherein during the execution of the operation associated with the first stimulus, for each node element of the first set of node elements, the corresponding one or more micro-overlay nodes are executed, whereas, for each node element of the second set of node elements, the one or more macro-overlay nodes associated with the first active node are executed.

4. The overlay system of claim 3,
wherein during the execution of the operation associated with the first stimulus, the processing circuitry is further configured to determine, for each node element of the first plurality of node elements, whether the corresponding node element is associated with at least one micro-overlay node, and
wherein the one or more macro-overlay nodes associated with the first active node are executed for each node element of the second set of node elements based on an absence of association of a micro-overlay node with the corresponding node element.

5. The overlay system of claim 3,
wherein the one or more macro-overlay nodes associated with the first active node are configured to store association data that is indicative of the association of at least one micro-overlay node with each of the first set of node elements, and
wherein the one or more macro-overlay nodes are executed for each node element of the second set of node elements based on an absence of association of a micro-overlay node with the corresponding node element.

6. The overlay system of claim 2, wherein the one or more macro-overlay nodes, associated with the first active node, are executed prior to the execution of the one or more micro-overlay nodes associated with each identified node element of the first set of node elements.

7. The overlay system of claim 2, wherein the one or more macro-overlay nodes, associated with the first active node, are executed after the execution of the one or more micro-overlay nodes associated with each identified node element of the first set of node elements.

8. The overlay system of claim 2,
wherein the first active node and the first set of macro-overlay nodes associated therewith constitute a first executable active node, and
wherein the first executable active node is configured to maintain the first set of macro-overlay nodes, in the executable graph-based model.

9. The overlay system of claim 8, wherein the first executable active node is further configured to maintain a first plurality of micro-overlay nodes associated with the first active node, in the executable graph-based model.

10. The overlay system of claim 8,
wherein each node element, of the first set of node elements, and at least one micro-overlay node associated therewith constitute an executable node element,
wherein the first executable active node is further configured to maintain a first set of micro-overlay nodes of a first plurality of micro-overlay nodes associated with the first active node, in the executable graph-based model, and
wherein one or more executable node elements, of the first active node, are configured to maintain a second set of micro-overlay nodes of the first plurality of micro-overlay nodes, in the executable graph-based model.

11. The overlay system of claim 1, wherein each node element, of the first set of node elements, and at least one micro-overlay node associated therewith constitute an executable node element that is configured to maintain the corresponding micro-overlay node, in the executable graph-based model.

12. The overlay system of claim 1, wherein the plurality of node elements comprise at least two of a group consisting of a unique identifier, a version identifier, a namespace, a name, a set of icons, a set of labels, an alternate identifier, a set of attributes, metadata, a node configuration, a node configuration extension, and node configuration strategies.

13. The overlay system of claim 1,
wherein at least one node element, of the first set of node elements, corresponds to an attribute,
wherein an attribute value object is associated with the attribute, and
wherein at least one micro-overlay node is associated with the attribute value object.

14. The overlay system of claim 13,
wherein during the execution of the operation associated with the first stimulus, the processing circuitry is further configured to identify (i) at least a first attribute value object associated with the first set of node elements based on the first context of the first stimulus and (ii) at least a first micro-overlay node associated with the first attribute value object, and
wherein the processing circuitry executes the operation associated with the first stimulus further based on the first attribute value object and the first micro-overlay node.

15. The overlay system of claim 1, wherein each active node of the plurality of active nodes corresponds to one of a group consisting of a vertex node, an edge node, a role node, a micro-overlay node, and a macro-overlay node.

16. The overlay system of claim 1, wherein at least one active node, of the plurality of active nodes, corresponds to an edge node with at least one role element being associated with the edge node, and wherein the role element corresponds to a node element of the corresponding active node.

17. The overlay system of claim 1, wherein each of the plurality of active nodes and the associated set of micro-overlay nodes comprises a node template that corresponds to a predefined node structure and a node instance that corresponds to an implementation of the node template.

18. The overlay system of claim 1, wherein the first stimulus corresponds to one of a group consisting of a command and a query.

19. The overlay system of claim 1, wherein prior to the execution of the operation associated with the first stimulus, the processing circuitry is further configured to load, in the executable graph-based model, one of a group consisting of (i) the first active node that comprises the first set of node elements and (ii) the one or more micro-overlay nodes associated with each identified node element, with corresponding data and processing logic.

20. A method, comprising:
receiving, by processing circuitry of an overlay system, a first stimulus associated with the overlay system,
wherein an executable graph-based model, stored in a storage element of the overlay system comprises:
a plurality of active nodes, where each active node comprises a plurality of node elements; and
a plurality of micro-overlay nodes associated with each active node of the plurality of active nodes, such that each micro-overlay node is associated with at least one node element, of the plurality of node elements, to extend functionality of the corresponding node element;
identifying, by the processing circuitry, in the executable graph-based model, based on a first context of the first stimulus, at least a first active node;

identifying, by the processing circuitry, based on the first context of the first stimulus, (i) a first set of node elements from a first plurality of node elements of the first active node, and (ii) one or more micro-overlay nodes associated with each identified node element, that are required for processing of the first stimulus; and executing, by the processing circuitry, an operation associated with the first stimulus based on the identified first set of node elements and the identified one or more micro-overlay nodes associated with each identified node element.

* * * * *